(12) United States Patent
Ettrup et al.

(10) Patent No.: US 11,564,624 B2
(45) Date of Patent: Jan. 31, 2023

(54) DEVICE AND METHOD FOR PROVIDING A MEASURE OF A CIRCUMFERENCE OF A BODY PART

(71) Applicant: Specialbandager.DK A/S, Bagsværd (DK)

(72) Inventors: Jens Ettrup, Bagsværd (DK); Henrik Harboe, Fårevejle (DK)

(73) Assignee: SPECIALBANDAGER.DK A/S, Bagsvaerd (DK)

( * ) Notice: Subject to any disclaimer, the term of this patent is extended or adjusted under 35 U.S.C. 154(b) by 383 days.

(21) Appl. No.: 16/068,789

(22) PCT Filed: Jan. 13, 2017

(86) PCT No.: PCT/DK2017/050004
§ 371 (c)(1),
(2) Date: Jul. 9, 2018

(87) PCT Pub. No.: WO2017/121434
PCT Pub. Date: Jul. 20, 2017

(65) Prior Publication Data
US 2019/0021660 A1    Jan. 24, 2019

(30) Foreign Application Priority Data

Jan. 13, 2016  (DK) .................................. 201670014

(51) Int. Cl.
*A61B 5/00* (2006.01)
*A61B 5/107* (2006.01)

(52) U.S. Cl.
CPC .......... *A61B 5/4878* (2013.01); *A61B 5/0004* (2013.01); *A61B 5/107* (2013.01);
(Continued)

(58) Field of Classification Search
CPC ..... A61B 5/107; A61B 5/1073; A61B 5/4878; A61B 5/6804; A61B 5/6831; A61B 2562/0261; H05K 1/0283; A41D 13/1281
See application file for complete search history.

(56) References Cited

U.S. PATENT DOCUMENTS

| 8,948,839 B1 | 2/2015 | Longinotti-Buitoni et al. |
| 2005/0054941 A1 | 3/2005 | Ting et al. |

(Continued)

FOREIGN PATENT DOCUMENTS

| CN | 101039641 A | 9/2007 |
| CN | 101087998 A | 12/2007 |

(Continued)

OTHER PUBLICATIONS

Cai et al.: "Super-stretchable, Transparent Carbon Nanotube-Based Capacitive Strain Sensors for Human Motion Detection", Scientific Reports, vol. 3, No. 1, Oct. 25, 2013.

(Continued)

*Primary Examiner* — Devin B Henson
*Assistant Examiner* — H. Q. Nguyen
(74) *Attorney, Agent, or Firm* — Dinsmore & Shohl LLP

(57) ABSTRACT

The present disclosure relates in general to a device and a method for providing a measure of a circumference of a body part. More specifically, the present disclosure relates to how to provide a measure of a circumference of a body part, wherein the body part may have swelled, such that it for example can be observed whether the body part swells further or less. Most specifically, the swelled body part may be swelled due to oedema and/or lymphoedema.

23 Claims, 22 Drawing Sheets

(52) U.S. Cl.
CPC .......... *A61B 5/1073* (2013.01); *A61B 5/6804* (2013.01); *A61B 5/6831* (2013.01); *A61B 2562/0261* (2013.01)

(56) References Cited

U.S. PATENT DOCUMENTS

| | | | |
|---|---|---|---|
| 2006/0084855 A1* | 4/2006 | Teschner | A61B 5/0536 600/390 |
| 2012/0078127 A1* | 3/2012 | McDonald | A61B 5/11 600/508 |
| 2013/0338472 A1* | 12/2013 | Macia Barber | A61B 5/6804 600/388 |
| 2014/0052028 A1* | 2/2014 | Wright | A61B 5/1073 600/592 |
| 2014/0296749 A1 | 10/2014 | Reid, Jr. et al. | |
| 2014/0343391 A1* | 11/2014 | Korkala | A61B 5/0408 600/393 |
| 2015/0143601 A1 | 5/2015 | Longinotti-Buitoni et al. | |
| 2015/0201856 A1* | 7/2015 | Stork | A61B 5/01 600/384 |
| 2016/0015297 A1* | 1/2016 | Strauss | A61B 5/1073 600/587 |
| 2017/0055921 A1* | 3/2017 | Martin | A61B 5/1135 |

FOREIGN PATENT DOCUMENTS

| | | |
|---|---|---|
| CN | 201469257 U | 5/2010 |
| EP | 3015065 A1 | 5/2016 |
| JP | 2013508002 A | 3/2013 |
| JP | 2015532841 A | 11/2015 |
| KR | 20080073531 A | 8/2008 |
| KR | 101573043 B1 | 12/2015 |
| WO | WO-2004/093763 A1 | 11/2004 |
| WO | WO-2004/100784 A2 | 11/2004 |
| WO | WO-2013/179670 A1 | 12/2013 |
| WO | 2014/204323 A1 | 12/2014 |
| WO | 2014/206379 A1 | 12/2014 |
| WO | WO-2015/002267 A1 | 1/2015 |
| WO | 2015/022671 A1 | 2/2015 |
| WO | 2015077838 A1 | 6/2015 |
| WO | 2015156174 A1 | 10/2015 |

OTHER PUBLICATIONS

Merritt, C. R. et al.: "Textile-Based Capacitive Sensors for Respiration Monitoring", IEEE Sensors Journal, IEEE Service Center, New York, NY, US, vol. 9, No. 1, Jan. 1, 2009, p. 71-78.

La'Toyah Christie-Ornstrup: "Edema Stocking", Jan. 28, 2013, XP055355372, Retrieved from the Internet: URL:http://www.edema.dk/wp-content/uploads/2013/01/Edema_Stocking_researchers.pdf (retrieved on Mar. 15, 2017).

FabricLink's award for 2013-2014 Tom 10 innovations: https://www.fabriclink.com/consumer/TopTen-2013.cfm.

Filippidou et al., "A flexible strain sensor made of graphene nanoplatelets/polydimethylsiloxane nanocomposite", Microelectronic Engineering 142, 2015, p. 7-11.

Hirata et al.: "The flexible interface using a stretch sensor", Procedia Manufacturing 3, 2015, p. 845-849.

Ohmatex ApS: "White paper on smart textile garments and devices: a market overview of smart textile wearable technologies.", 2014.

Thomsen and Júlíusdóttir, "Design, construction and validation of a knee brace angle measuring device for online monitoring", Department of Health Science and Technology, Aalborg Universitet, 2014.

Webarchive excerpt excerpt, Nov. 28, 2015, http://web.archive.org/web/20151128071840/http://www.fabriclink.com/Consumer/TopTen-2013.cfm.

Yu et al., "Foot edema simulation and monitoring using dielectric electroactivepolymer sensors", Sensors and Actuators A225, 2015, p. 33-40. (https://doi.org/10.1016/j.sna.2015.02.005).

* cited by examiner

DEVICE AND METHOD FOR PROVIDING A MEASURE OF A CIRCUMFERENCE OF A BODY PART

FIELD OF INVENTION

The present disclosure relates in general to a device and a method for providing a measure of a circumference of a body part. More specifically, the present disclosure relates to how to provide a measure of a circumference of a body part, wherein the body part may have swelled, such that it for example can be observed whether the body part swells further or less. Most specifically, the swelled body part may be swelled due to oedema and/or lymphoedema.

BACKGROUND OF INVENTION

Lymphoedema may manifest as swelling of one or more body parts. Swelling may also affect other body parts, for example the head and neck. Lymphoedema is the result of accumulation of fluid in the tissue spaces. Lymphoedema may produce significant physical and psychological morbidity. Pain and discomfort are frequent symptoms and increased susceptibility to acute cellulitis can result in frequent hospitalization and long term dependency on antibiotics. Lymphoedema is a chronic condition that is not curable at present, but may be alleviated by appropriate management—if ignored, it can progress and become difficult to manage.

One way of managing lymphoedema is to reduce swelling through a combination of compression, for example using bandage or compression garments, such as stockings, masks, shirts and waistcoats, and exercise with or without lymphatic massage (for example manual lymphatic drainage, simple lymphatic drainage or intermittent pneumatic compression).

Successful management of lymphoedema relies today on patients and doctors playing an active role.

In particular when bandage and/or compression garments are used, the patient or the doctor must first remove the compression bandage or compression garments, assess the body part that is swelled, and then apply a new bandage or compression garments to the swelled body part, taking the assessment into account.

The process for management of oedema and/or lymphoedema requires today a lot of work and material in bandage.

Thus, there is a need for a device that is able to improve the management of oedema and/or lymphoedema.

SUMMARY OF INVENTION

The present disclosure provides a device and a method that is able to improve the management of oedema and/or lymphoedema.

In a first aspect of the invention, there is provided a device configured for providing a measure of a circumference of a body part, comprising: a first elastic support material configured for being placed around and/or on the body part, the first elastic support material having a first elastic support material length defining an longitudinal axis, a first elastic support material width defining a vertical axis and a first elastic support material thickness defining a lateral axis; one or more electrically conducting layer(s) located above and/or or below at least a part of the first elastic support material along at least a part of the longitudinal axis and/or along at least a part of the vertical axis, wherein the electrically conducting layer(s) is/are stretchable; a measuring unit that is electrically connected to the one or more electrically conducting layer(s), wherein the measuring unit is configured for measuring an electric property related to the one or more electrically conducting layer(s), the electric property being related to the measure of the circumference of the body part.

In addition hereto, the device comprises in one embodiment at least one additional layer located above and/or below the one or more electrically conducting layer(s), wherein the at least one additional layer is elastic, and wherein the at least one additional layer is configured for being in contact with the first elastic support material, thereby encapsulating the one or more electrically conducting layer(s) in-between the first elastic support material and the at least one additional layer, and such that at least part of the one or more electrically conducting layer(s) is/are able to move relative to the first elastic support material and/or relative to the at least one additional layer, and/or the one or more electrically conducting layer(s) has/have an electrically conducting layer length that is able to be stretched at least 20% relative to its relaxed state, and/or the measure of the circumference of the body part is a change in circumference of the body part, and/or the first elastic support width, in a relaxed state, may be between 1 cm and 16 cm and/or the one or more electrically conducting layer(s) has/have a conducting layer width that, in a relaxed state and along a vertical axis, is between 2 mm and 80 mm.

In some embodiments, at least part of the one or more electrically conducting layer(s) is/are fixed to the first elastic support material and/or to the at least one additional layer.

The inventors of the present invention have realized that in order to place one or more electrically conducting layer(s) around and/or on the body part, and when the measure of the circumference of a body part is to be provided, it is important that there is a first elastic support material that is able to at least hold the one or more electrically conducting layer(s) in place. Thus, although one or more electrically conducting layer(s) have been disclosed as suitable for clothing, garments, etc., the inventors have found that such materials on their own are not suitable to be placed around a given place on the body part when the measure of the circumference of a body part is to be provided. When the measure of the circumference of a body part is to be provided, it is very important that the one or more electrically conducting layer(s) stay in that place that define the circumference of a body part. Therefore, one role of the first elastic support material is to hold the one or more electrically conducting layer(s) in place.

One way to place the first elastic support material around the body part may be to simply wrap the first elastic support material around the body part, for example such that the length of the first elastic support material, or part thereof, defines the circumference of the body part, or at least approximately the circumference of the body part. Nevertheless, the longitudinal axis is curved around the body part. Furthermore, the elastic support material is per se elastic, and the length is therefore stretchable from its relaxed state. Thus, the longitudinal axis is to be defined by the length of the elastic support material when it is not placed on the body part, and in a relaxed state.

The longitudinal axis may be defined as when the layer material is not placed on the body part, and not rolled up, or wrapped around the body part, but rather for example when placed on a flat surface, such as a table. In another embodiment, the first elastic support material is a garment, for example such as a compression garment, in particular a compression stocking. In such cases, the longitudinal axis may be defined as when the compression garments is also placed on a flat surface, such as a table. The length is, in this case, the circumference of the compression garments in a relaxed state around a given place.

In one embodiment, the first elastic support material is either a layer material, such as tape, responsible for holding the one or more electrically conductive layer(s) in place or a layer material such as bandage or compression garments, responsible for applying pressure to the body part. Compression garments as herein referred to may for example be stockings, masks, shirts and waistcoats.

Compression bandages and compression garments are meant to be worn twenty four hours a day, every day to maintain edema reduction and must be replaced on a regular basis. Depending on the therapist's discretion, a compression garment may be custom-fit or purchased in over-the-counter, i.e. in standard sizes. Some people will require custom-made compression garments and it is important that these garments fit correctly.

Compression bandage or garment materials are typically characterized by elastic, long-stretch, inelastic, or short-stretch materials. The terms elastic and long-stretch (elastic/long-stretch) bandages are often used synonymously, as are inelastic and short-stretch (inelastic/short-stretch) bandages. Extensibility differs markedly between these two basic types. Extensibility refers to the degree to which the bandage can be stretched when pulled. Generally, an elastic/long-stretch bandage has a maximal extensibility greater than 100%, whereas an inelastic/short-stretch bandage has a maximal extensibility of less than 100%.

As discussed below the two different types of compression bandage and garment material may be suitable for different types of oedema and patients. Furthermore, even material within the same category, for example inelastic material, from different commercial providers may have different degrees of elasticity and wearability.

Gradient compression, i.e. a pressure gradient decreasing towards the heart is the basic principle for compression therapies. Roughly 60% to 80% of the body's total blood volume resides in the venous circulation. During walking or weight shifting, calf-muscle contraction is the primary means of returning blood to the heart through the veins. Pressure generated from the calf muscle can reach up to 300 mm Hg, propelling 60% of venous volume proximally with each contraction. Short-stretch bandages create an external force against calf-muscle contraction. They cause generation of inward pressure because they don't allow calf muscles to bulge outward when they contract and shorten.

It is known that placing a first elastic support material, for example such as tape, bandage, compression garments, around a body part that is swelled, for example due to oedema and/or lymphoedema, may have a positive impact on the swelling such that some or all of the swelling disappears. Thus, one advantage of providing the first elastic support material is to provide a healing effect to patients, in particular patients with oedema and/or lymphoedema.

The first elastic support material may not necessarily stick to the body part, when placed around the body part. As long as the first elastic support material is able to be stretched such as to provide a proper restoring force, it may be possible to place the first support material on/around the body part by exploiting the restoring force of the first elastic support material. A compression garments, when matched to the body part, is indeed made such that restoring force is able to keep the compression garments, and thereby, by using the present invention, keep the one or more electrically conducting material layer(s) in place on the body part.

By the present invention it is to be understood, that the one or more electrically conducting material layer(s) may be placed on one side of the first elastic support material. An advantage of the present invention is that the one or more electrically conducting material layer(s) for example may be placed in the order:
  a) body part; and
  b) one or more electrically conducting material layer(s); and
  c) first elastic support material; and/or
in the order:
  a) body part,
  b) first elastic support material; and
  c) one or more electrically conducting material layer(s).

Thus, the one or more electrically conducting material layer(s) may be on the inside and/or on the outside of the first elastic support material. A second elastic material may further be placed around the body, such that a) and c) are below a second elastic material. For example, the second elastic material may be a bandage or a compression garment.

In one embodiment of the first aspect, it is to be understood that the first elastic support material configured for being placed around and/or on the body part may also mean that the first elastic support material configured is configured to be placed around and/or on a second elastic support material in contact with the body part. The reason is that the circumference can still be provided. For example, when the second elastic support material is placed around the body part before the first elastic support material, then the circumference of the body includes the thickness of the second elastic support material. The second elastic material may for example be a bandage.

Since the one or more electrically conducting material layer(s) may be on the inside and/or on the outside of the first elastic support material as just described, it is also possible to place the one or more electrically conducting material layer(s) in the order:
  a) body part; and
  b) second elastic support material;
  c) one or more electrically conducting material layer(s); and
  d) first elastic support material; and/or
in the order:
  d) body part;
  e) second elastic support material;
  f) first elastic support material; and
  g) one or more electrically conducting material layer(s).

Several other layer(s) may be placed between any of the materials and/or layers. The above embodiments are just examples.

One advantages of the present invention, is thus the flexibility in where the one or more electrically conducting material layer(s) may be placed. As can be seen from the orders of placement as above, the one or more electrically conducting material layer(s) need not to be in direct contact with the body part. The reason for this is, as previously also described, that in all cases, the measure of a circumference of a body part may be provided.

As described in the first aspect of the present invention, the one or more electrically conducting layer(s) may be above and/or below at least a part of the first elastic support material along at least a part of the longitudinal axis and/or along at least a part of the vertical axis. Thereby it is understood that when the first elastic support material is placed around the body part, in particular with the length of the first elastic support material, follows the body part around, the one or more electrically conducting layer(s) has a length that is able to be stretched. The change in length of the one or more electrically conducting layer(s) changes the electric property of the one or more electrically conducting layer(s), such that a given length of the one or more electrically conducting layer(s) specifies a given length and/or circumference of a body part.

In relation to the circumference of the body part, in particular when managing oedema and/or lymphoedema, it may not be necessary to obtain an exact circumference of the body part. What may be more important is the change in the circumference of the body part. Thus, according to one embodiment of the first aspect of the present invention, the measure of the circumference of the body part may in addition or as an alternative be a change in circumference of the body part.

The progress of swelling may then be monitored by observing the change in circumference of the body part. The swelling may get worse, thereby increasing the circumference of the body part, or the swelling may get better, thereby decreasing the circumference of the body part.

As described, the measuring unit is configured for measuring an electric property related to the one or more electrically conducting layer(s), the electric property being related to the measure of the circumference of the body part. As will be described in the detailed description, the circumference may be linearly dependent on the electric property. Thus, in one embodiment, the measure of the circumference of the body part, or simply the length of the one or more electrically conductive layer(s) may be related as a linear relationship, such that the length L, is proportional to a constant, C, with the addition of a proportionality factor P multiplied with the electric property E being measured. Thus, in one embodiment, in order to relate the electric property to the measure of the circumference, there must be a determination of C and P. The constant C may depend on the length of the one or more electrically conductive layer(s) and/or another material(s) extending from the one or more electrically conducting layer(s) or from the first elastic support material along the longitudinal axis. The proportionality factor, P, may depend on the electric property being measured, and how the device is manufactured, i.e. P may depend on materials properties of one or more electrically conductive layer(s) and/or other materials, for example between the one or more electrically conductive layer(s). In other words, when stated that the measuring unit is configured for measuring an electric property related to the one or more electrically conducting layer(s), the electric property being related to the measure of the circumference of the body part, there may be at least two parameters, such as C and P, that may need to be pre-defined, and may be dependent on how the device is made and what the measuring unit is measuring.

According to a second embodiment of the first aspect of the present invention, the device may also comprise at least one additional layer located above and/or below the one or more electrically conducting layer(s), wherein the at least one additional layer is elastic, and wherein the at least one additional layer is configured for being in contact with the first elastic support material. Such two layers may encapsulate the one or more electrically conducting layer(s) such that at least part of the one or more electrically conducting layer(s) is/are able to move relative to the first elastic support material and/or relative to the at least one additional layer. By this embodiment, the inventors have found that the measurement of the one or more electrically conducting layer(s) may be more precise than if the one or more electrically conducting layer(s) is/are attached to first elastic support material. The reason is that the measurement in the latter case becomes dependent on the first elastic support material. By the present invention, the measurement is independent of the first elastic support material, and provides thus for a more accurate device.

Further, in a third embodiment of the first aspect of the present invention, the one or more electrically conducting layer(s) may have an electrically conducting layer length that is able to be stretched at least 20% relative to its relaxed state. By this embodiment there is first of all provided a measurement of the circumference, where the circumference can increase at least 20%, for example if the first support material is attached to the body part such that the first elastic support layer, and thereby also the one or more electrically conducting layer(s), is/are approximately is in a relaxed state. Secondly, there is provided a measurement of the circumference, where the circumference can decrease after the first elastic support material has been placed around the body part and/or the second elastic support material, for example if the one or more electrically conducting layer(s) has/have been pre-stretched up to at least 20% in the process of placing the first elastic support material on the body part and/or the second elastic support material. As previously described, the body part, i.e. the circumference, is able to get smaller when for example swelling decreases.

In a fourth embodiment of the first aspect of the present invention, the first elastic support width, in a relaxed state, may be between 1 cm and 15 cm and/or the one or more electrically conducting layer(s) has/have a conducting layer width that, in a relaxed state and along a vertical axis, is between 2 mm and 80 mm. The conductive layer width may also be between 1 cm and 15 cm, such as between 2 cm and 4 cm, such as between 2 cm and 6 cm, such as between 2 cm and 8 cm or such as between 2 cm and 10 cm. The elastic support material ranges as here defined may facilitate that a swelled body part experiences a pressure that is not limited to a small area, since this could have no or only little effect on a swelled body part. Further, a smaller first elastic support width could cause pain on a swelled body part. Even further, a smaller width could cause a swelled body part to swell outside the one or more electrically conducting layer(s) and/or the first elastic support material, which is not ideal.

In a second aspect of the invention, there is provided a method for providing a measure of a circumference of a body part, comprising the steps of: providing a device configured for providing a measure of a circumference of a body part, the device comprising at least a first elastic support material; and providing a second elastic support material; and placing the first elastic support material around and/or on the body part, placing the second elastic support material around and/or on the body part; wherein the step of placing the second elastic support material is done after the first support material is placed around the body part, such that the second elastic support material is placed around and/or on the first support material, or before the first support material is placed around the body part; such that the first elastic support material is placed around and/or on the second support material; or at the same time as the first elastic support material is placed around the first support material, such that the first support material and second support material are pre-attached to each other; and monitoring the measure of the circumference of the body part after the first and second elastic support material have been placed.

In one embodiment, the device as described in the second aspect of the invention is a device according to the first aspect of the invention.

Since the present invention relates to managing oedema and/or lymphoedema, and/or swelling in general, an advantage of the present invention, is that it provides for a device and a method to for example determine when a first support material and/or a second support material needs to be replaced by a new first support material and/or a second support material.

By using a device according to the present invention, and/or the method according to the present invention, it may be possible to measure the circumference under a bandage. Based on the measure of the circumference, it may be determined whether or not the bandage needs to be replaced or if it can stay on. Thus, the present invention provides for a device and/or a method that reduces the cost of managing patient with swelling. The present invention is able to reduce cost in terms of bandage material, but also in terms of time—time related to assessing the body part, and time related to replacing for example a bandage.

Further details of the present invention are described below.

DESCRIPTION OF DRAWINGS

FIG. 11 is a schematic representation of the layers that may be provided in embodiments of the present invention.

DETAILED DESCRIPTION OF THE INVENTION

Figure 1:
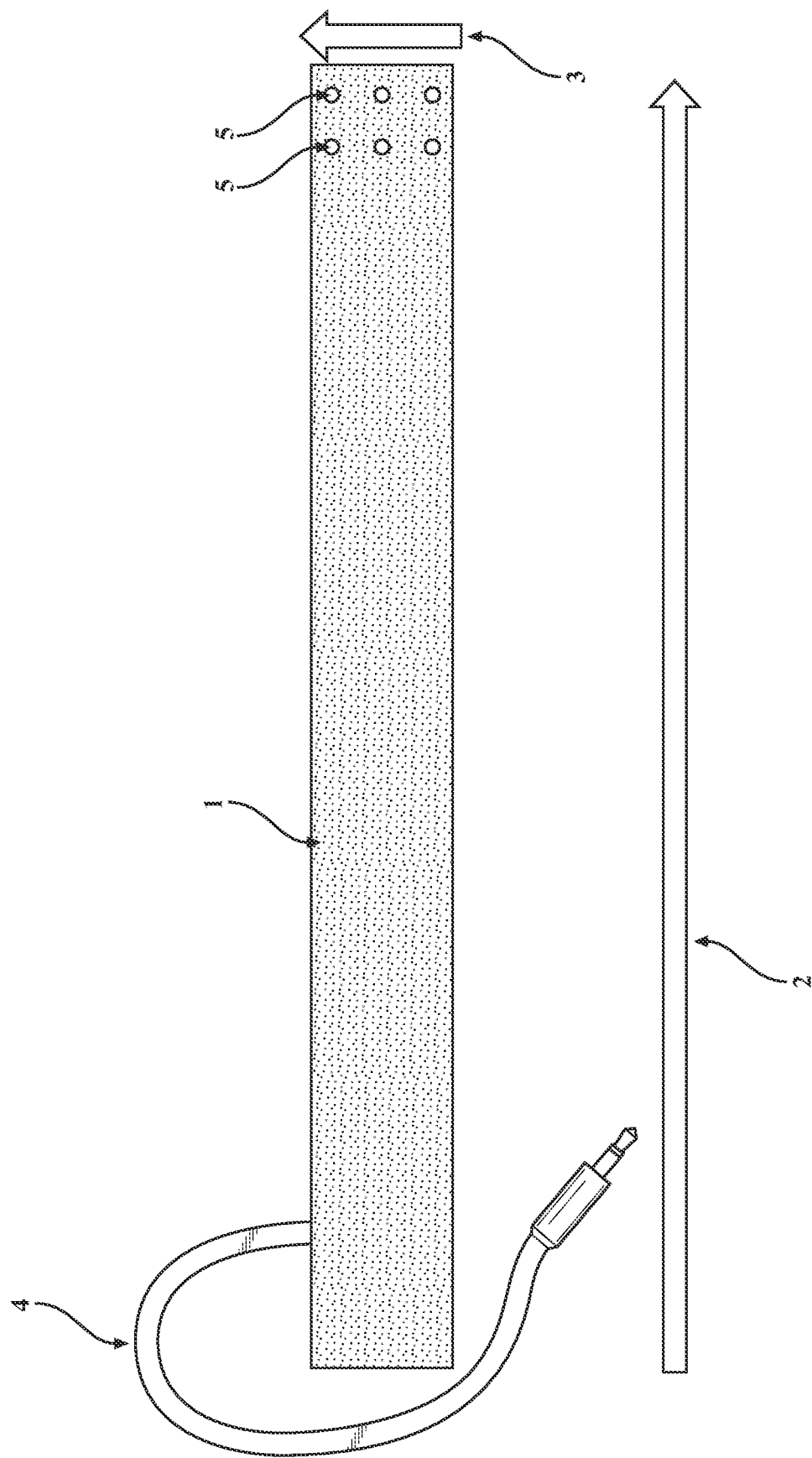
FIG. 1 shows an embodiment of the device according to the first aspect of the present invention.

As previously described, the measure of the circumference of the body part may be a change in circumference of the body part. Alternatively, and/or additionally, the measure of the circumference of the body part may be a part of the circumference of the body part. The device and method as discloses herein is particular suited for management of swelled body part.

The body part as herein described may generally be referred to as a limb. However, as also described in the background of the invention, the body part may be the trunk or the head. The body part may also be a leg or a part thereof, a foot or a part thereof, an arm or a part there, and/or a hand or a part thereof.

As has also been described in the summary of the invention, or at least referred, the first elastic material may be a bandage and/or a compression garments. Also, the second elastic support material may be a bandage or a compression garments.

In one embodiment of the device, the device further comprises one or more non-elastic support material(s) extending from the one or more electrically conducting layer(s) or from the first elastic support material along the longitudinal axis, and/or along the vertical axis. In that way, it will be possible to measure only a part of the circumference. However this may be sufficient for providing a measure of the circumference of the body part. Having non-elastic support material may further lower the cost of the device.

In another embodiment of the device, the device comprises attachment means in both ends of the longitudinal axis, such that both ends can be attached to each other. For example, the attachment means may be attached to the one or more non-elastic support material(s). Attachment means as here disclosed may facilitate easy placement of the device around and/or on the body part.

Transmitting Unit, Receiving Unit and Control Unit

In one embodiment of the device, the device further comprises a transmitting unit configured for transmitting the measure of the circumference of the body part to a receiving unit. The receiving unit may receive data with the measure of the circumference of the body part by wireless communication and/or by wired communication. Wireless communication may be via technologies such as Bluetooth or near field communication.

In some embodiments, the receiving unit may comprise a data storing unit. In one embodiment, the data storing unit is a hard drive, for example a portable drive such as a solid state drive, or an optical drive, for example connected via USB in the case of wired communication. On other embodiments, the receiving unit, having a data storing unit, is integrated with the measuring unit.

In a preferred embodiment of the device, the data storing unit may also be removably attached to the first elastic support. This may facilitate an integrated solution of the device, but also a solution, where it may be possible to take the data storing unit from the first elastic support material, thereby be able to plug the data storing unit into an external data accessing unit, such as a computer or a handheld device, thereby accessing the data on the data storing unit.

In some embodiments of the device, the transmitting unit and/or the measuring unit and/or the receiving unit are integrated into one unit.

In another preferred embodiment of the device, the receiving unit is detached from the first elastic support. This may for example be of importance, if the device is placed under a bandage, or simply if the receiving unit does not need to be a removably attached unit. For example, the receiving unit may be a computer, a server or a handheld device. By accessing any of these receiving units, it is possible to get access to the data with the measure of the circumference of the body part. Alternatively, and/or additionally, the measure of the circumference of the body part may be used to notify the patient of his/her status of swelling and/or de-swelling. For example, the receiving unit may be configured for processing the data from the device according to the present invention, and configured for providing a notification based on the processed data, such as a green output or a red output.

In a most preferred embodiment of the device, the device further comprises a control unit configured to control the length of the one or more electrically conducting layer(s) along the longitudinal axis, for example by receiving the measure of the circumference of the body part directly from the transmitting unit. The one or more electrically conducting layer(s) may be configured as an actuator, such that when the controller receives input, for example based on the measure of the circumference of the body, the control unit may send an electrical signal to the one or more electrically conducting layer(s), such that the length is shortened. Thus, by having the control unit, the present invention provides for a feed-back mechanism based, i.e. treatment that is based on tightening the first elastic support material further to the body part when it receives instructions based on output from the measuring unit. In other words, the present invention may provide an automatic and self-adaptable support material, for example such as a bandage and/or a compression garments.

Elastic Support Material

In one embodiment of the device, the first elastic support material is configured for being attached to the skin of the body part. The first elastic support material may for example comprise cotton, acrylic fibres, be breathable and be water proof. In most preferred embodiments, the first elastic support material comprises of polyurethane fibres, for example elastane.

In other most preferred embodiments, the first elastic support material is configured with a smooth surface that is defined by its coefficient of friction, wherein the coefficient of friction between is between a value of 0.2 and 0.4, and wherein the coefficient of friction is defined relative to a surface of steel.

The coefficient of friction may be measured using a standard friction test, using for example a commercial system known as the KES system—a system developed by the Hand Evaluation and Standardization Committee of the Textile Machinery Society, Japan. In particular, the coefficient of friction may be measured using the KES-FB4.

The coefficient of friction depends on many factors, including temperature and moisture. Thus, the coefficient of friction as herein referred to may be for textiles that are conditioned at a relative humidity at 65±2% and a temperature of 22±1° C.

Friction tests may involve sliding a probe on the test material with a constant force, whereby a coefficient of friction curve is given by the ratio of the force registered in a transducer (attached to the probe) to the normal force. The mean value of the coefficient of friction is thus the average height of the curve.

Accordingly, the coefficient of friction as referred to herein may be referred to as the kinetic coefficient of friction. Furthermore, the coefficient of friction as referred to herein may be referred to as the mean kinetic coefficient of friction.

It is clear that the coefficient of friction also depends on the probe material. For standardized measurements, the probe is made of steel.

However, it may be possible to provide a coefficient of friction measurement of textiles on skin, for example by rubbing a measuring probe with a multi-component force sensor on a part of the skin, whereby the normal and tangential forces can be measured in order to determine the coefficient of friction. It has been found that different parts of the body, i.e. different skin parts of the body, changes the coefficient of friction measurement of a textile. Furthermore, coefficient of friction when measured on skin is very dependent on skin type and varies from person to person, thus making it difficult to provide a standard measurement.

For this reason, a steel probe as used to define the coefficient of friction enables a standardized measurements for coefficient of friction.

As explained herein, the first elastic support material may be in contact with the skin, since it may be the layer of the device that can be in contact with the patient.

The inventors have found that by having the first elastic support material configured with a smooth surface that is defined by its coefficient of friction, wherein the coefficient of friction between the smooth surface and a surface of steel is between 0.2 and 0.4, enables that the device is to be placed on the skin such that the device does not change its placement on the body part. Furthermore, the coefficient of friction between 0.2 and 0.4 as defined above enables that the device is to be placed on the skin such that the device defines a contact surface that is easily adapted to the body part without the first support material being wrinkled, for example by not sticking to the body part.

As explained herein, the first elastic support material may also be in contact with a second elastic material such as a bandage.

The inventors have found that by having the first elastic support material configured with a smooth surface that is defined by its coefficient of friction, wherein the coefficient of friction between the smooth surface and a surface of steel is between 0.2 and 0.4, enables that the device is to adapt to the body part without the support material being wrinkled, for example by not sticking to a second elastic support material such as a bandage.

In other words, the coefficient of friction between 0.2 and 0.4 as defined above, is selected to enable the surface of the first elastic support material to adapt to the body part such that it does not stick to either the body part or a second elastic support material. The inventors have found that this particular coefficient of friction provides an optimal value. If the value was lower, the device would get misplaced. If the value was higher, the device would wrinkle. Thus, the inventors have found that the coefficient of friction between 0.2 and 0.4 as defined above facilitates a very precise measurement of the circumference of the body part.

In a second embodiment of the device, the first elastic support material length, in a relaxed state, is between 15 cm and 85 cm. Thereby should it be configured to fit various body parts of various sizes.

In a third embodiment of the device, the first elastic support material is a circular band configured to fit around a body part. The circular band may be made from the device according to the present invention, for example by sewing the two ends of the first elastic support material together. In other words, the first elastic support material or at least a part of it, may be sewable to form a circular band.

In some embodiments, the first elastic support material or at least a part of it, is gluable. Such an embodiment may provide for the transmitting unit to be attached to the device.

Most preferably, a kit comprises a plurality of devices, each device configured for providing a measure of a circumference of a body part according to the first aspect of the invention. The plurality of devices, may be up to four devices, each device being configured such that the first elastic support material is circular as just described, and each device with different first elastic support material length. In this way, a first device having one circumference, may fit to some patients having swelled legs with a first circumference interval, while another device having a second circumference, may fit to other patients having a second circumference interval. The second circumference may for example be larger than the first circumference interval. In relation hereto, it may also be such that if a patient having the second device, experience a de-swelling, that patient may then be able fit the first device, whereby a more efficient measurement and/or treatment is achieved.

As also described earlier, the elastic support width, in a relaxed state, may be between 1 cm and 16 cm, such as between 2 cm and 15 cm.

The first elastic support material length is able to be stretched at least 20% relative to its relaxed state. By this embodiment there is first of all provided a measurement of the circumference, where the circumference can increase at least 20%, for example if the first support material is attached to the body part such that the first elastic support layer, and thereby also the one or more electrically conducting layer(s), is/are approximately is in a relaxed state. Secondly, there is provided a measurement of the circumference, where the circumference can decrease after the first elastic support material has been placed around the body part and/or the second elastic support material, for example if the one or more electrically conducting layer(s) has/have been pre-stretched up to at least 20% in the process of placing the first elastic support material on the body part and/or the second elastic support material.

In preferred embodiments, the first elastic support material length is able to be stretched up to 250% relative to its relaxed state, such as up to 40%, such as up to 60%, such as up to 80%, such as up to 100%, such as up to 120%, such as up to 150%, or such as up to 200%.

In most preferred embodiments, the first elastic support material is stretchable to the same degree as the one or more electrically conducting layer(s).

Electrically Conducting Layer(s)

The one or more electrically conductive layer(s) may be made from a material having a resistivity which is less than $10^{-2}$ Ω cm such as less than $10^{-4}$ Ω cm.

The one or more electrically conductive layer(s) may preferably be made from a metal or an electrically conductive alloy, e.g. from a metal selected from a group of silver, gold and nickel. Alternatively other suitable metals or electrically conductive alloys may be chosen.

The one or more electrically conductive layer(s) may be electrical tape, such as made of conductive acrylic with for example Nickel plated carbon scrim. The tape may be adhesive.

The one or more electrically conductive layer may have a thickness in the range of 0.01 μm to 0.1 μm, such as in the range of 0.02 μm to 0.1 μm, such as in the range of 0.08 μm to 0.1 μm.

A first conductor may be attached to the one or more electrically conductive layer(s) in a first connection point. The conductor may be formed as an elongated body like a traditional wire or cable. In another embodiment, the conductors may be formed as pouches being circular, oval, or of another shape suitable for establishing the electrically communication with electrically conducting layer(s). The conductor may be highly elastically deformable such that the length of the conductor may be varied, or the conductors may at least be flexibly bendable.

The one or more electrically conducting layer(s) may have an electrically conducting layer length that, in a relaxed state, is less than 90% relative to the elastic support length, such as less than 75%, such as less than 60%, such as less than 50%, such as less than 40%, such as less than 30%, such as less than 20%, or such as less than 10%. This may reduce cost of the electrically conducting layer length, and still provide a measure of the circumference of the body part.

The one or more electrically conducting layer(s) may have an electrically conducting layer length, in a relaxed state, between 2 cm and 85 cm.

The one or more electrically conducting layer(s) may have an electrically conducting layer width that, in a relaxed state and along the vertical axis, is between 2 mm and 80 mm, or between 2 cm and 15 cm.

The one or more electrically conducting layer(s) may have an electrically conducting layer length that is able to be stretched at least 20% relative to its relaxed state.

The one or more electrically conducting layer(s) may be stretchable to the same degree as the first elastic support material.

The one or more electrically conducting layer(s) may have an electrically conducting layer length that is defined by the body part such that when the first elastic support material is placed around and/or on the body part and/or on the second elastic support material in contact with the body part, the electrically conducting layer length is pre-stretched at least 20% relative to its relaxed state.

In one embodiment of the device, the one or more electrically conducting layer(s) are separated from each other along the vertical axis.

In another embodiment of the device, the one or more electrically conducting layer(s) are separated from each other along the longitudinal axis.

In a preferred embodiment of the device, the one or more electrically conducting layer(s) may be separated from each other along the lateral axis by having a stretchable film between two of said electrically conducting layers. The stretchable film defines that the electric property is the electric capacitance of the stretchable film. The capacitance of the stretchable film is proportional to an area, over which there is an overlap of the two electrically conducting layers, and inverse proportional to the distance between the two electrically conducting layers, i.e. inverse proportional to the thickness of the stretchable film. Thus, the capacitance is also proportional to the length of the electrically conducting layers. Hence, the longer the electrically conducting layers, the greater the capacitance. Thus, by swelling, the length and thereby the circumference increases, and accordingly, the capacitance increases.

In an alternative and/or additional embodiment of the device, the electric property is the resistivity of the electrically conducting layer(s). The resistivity is proportional to the length of the electrically conducting layer and inverse proportional to the cross-sectional area of the electrically conducting layer, i.e. thickness and the width of the electrically conducting layer. Hence, the longer the electrically conducting layers, the greater the capacitance. Thus, by swelling, the length and thereby the circumference increases, and accordingly, the resistivity increases.

A difference between the capacitance and the resistivity in relation to when the one or more electrically conducting layer is stretched, is that the capacitance is influenced by the change in thickness of the stretchable film, whereas the resistivity is influenced by the change in the thickness of the one or more electrically conducting layer.

If the thickness of the one or more electrically conducting layer(s) and the stretchable film may however be deformed in the same manner, there may not be a difference in how the measurement is proportional to the length. On the other hand, a stretchable film may be chosen such that it deforms in a different manner than that of the one or more electrically conducting layer(s), thereby providing advantages in measuring capacitance in comparison to measuring the resistivity, in particular because the capacitance can be made approximately linearly dependent on the length deformation of the one or more electrically conducting layer(s). Several features of the stretchable film are described in the following section.

Stretchable Film

By using a stretchable film between two layers, and measuring the capacitance, there is provided means for providing a dielectric electroactive polymer (EAP) structure, in particular when the stretchable film is a polymer. In preferred embodiments, the stretchable film is made of silicone.

In one embodiment of the present invention, the stretchable film is a polymer that may be made from a material having a resistivity larger than $10^{10}$ Ω cm.

Preferably, the resistivity of the dielectric material is much higher than the resistivity of the electrically conductive layer, preferably at least $10^{14}$-$10^{18}$ times higher.

The film structure may comprise any number of layers of an elastically deformable polymer film, e.g. one, two, three, four, or five layers of the elastically deformable film either adhesively joined or simply stacked above each other to form a laminated structure. The elastically deformable film may particularly be made from a dielectric material which herein is considered to cover any material which can sustain an electric field without conducting an electric current, such as a material having a relative permittivity, which is larger than or equal to 2. It could be a polymer, e.g. an elastomer, such as a silicone elastomer, such as a weak adhesive silicone or in general a material which has elastomer like characteristics with respect to elastic deformation. For example, Elastosil RT 625, Elastosil RT 622, Elastosil RT 601 all three from Wacker-Chemic could be used as a dielectric material.

In the present context the term 'dielectric material' should be interpreted in particular but not exclusively to mean a material having a relative permittivity which is larger than or equal to 2.

In the case that a dielectric material which is not an elastomer is used, it should be noted that the dielectric material should have elastomer-like properties, e.g. in terms of elasticity. Thus, the dielectric material should be deformable to such an extent that the composite is capable of deflecting and thereby pushing and/or pulling due to deformations of the dielectric material.

The film may have a thickness between 10 μm and 200 μm, such as between 20 μm and 150 μm, such as between 30 μm and 100 μm, such as between 40 μm and 80 μm.

In relation a setup with two electrically conducing layers, a first conductor may be attached to the first electrically conductive layer in a first connection point, and the second conductor may be attached to the second electrically conductive layer in a second connection point. The conductor may be formed as an elongated body like a traditional wire or cable. In another embodiment, the conductors may be formed as pouches being circular, oval, or of another shape suitable for establishing the electrically communication with one of the electrodes.

By having a stretchable film as described, in particular a dielectric electroactive polymer, it is clear the one or more electrically conducting layer(s) are configured as an actuator. Actuation is then caused by electrostatic forces between two electrodes which squeeze the polymer. Dielectric elastomers are capable of very high strains and are fundamentally a capacitor that changes its capacitance when a voltage is applied by allowing the polymer to compress in thickness and expand in area due to the electric field.

Thus, by using a stretchable film there is provided a device that is able to work as an artificial muscle.

Additional Layer

In one embodiment of the device, the device further comprises at least one additional layer located above and/or below the one or more electrically conducting layer(s), wherein the at least one additional layer is elastic, and wherein the at least one additional layer is configured for being in contact with the first elastic support material, thereby encapsulating the one or more electrically conducting layer(s) in-between the first elastic support material and the at least one additional layer, and such that at least part of the one or more electrically conducting layer(s) is/are able to move relative to the first elastic support material and/or relative to the at least one additional layer.

In another embodiment of the device, the at least one additional layer is identical to the first elastic support material. In preferred embodiments, the at least one additional layer is made of silicone.

In yet another embodiment of the device, the at least one additional layer has an additional layer width that, in a relaxed state and along the vertical axis, is between 1 cm and 16 cm.

In a preferred embodiment, the at least one additional layer is stretchable to the same degree as the first support material.

Measuring Unit

As previously described, in one embodiment, deformation in a polymer film, for example due to being stretched, changes the distances between two electrically conductive layers located on opposite surfaces of the film structure. This changes the capacitance, and the deformation can therefore be measured using the measuring unit.

In some embodiments, the measuring unit is integrated in the device such that the measuring unit is able to move relative to at least one of the layers, for example inside a drawstring hem. The drawstring hem may be located in the first elastic support material. Further, the drawstring hem may comprise an inner wall configured with a smooth surface, such that the measuring unit is able to smoothly move inside the drawstring hem.

In another embodiment of the device, the measuring unit is further configured for measuring an electric property related to the one or more electrically conducting layer(s), the electric property being related to temperature and/or moisture. For example, this could be achieved by measuring the resistivity of a single electrically conducting layer as it is known that resistivity is for example temperature dependent.

In most preferred embodiments, the measuring unit is configured for sampling at a sampling rate of less than 10 measurements per minute. Most preferably, the sampling rate is with one measurement per 5 seconds, corresponding to 12 measurements per minute. Most preferably, the sampling rate is with one measurement per 10 seconds, corresponding to 6 measurements per minute. Having a low sampling rate provides for a device that can last a long time. A long lasting device is important since the device is typically to be worn for several days. In some cases, the measuring unit is unable to be recharged, since it may be inaccessible, for example when placed under a bandage.

The measuring unit may be a printed circuit board, such as a flexible printed circuit board, known as a flex print.

In alternative or additional embodiments, the device further comprises a sensor to measure temperature and/or moisture.

In another alternative or additional embodiment, the device further comprising an accelerometer, for example to be able to monitor the activity of the person wearing the device.

Preferably, the measuring unit may be attached to the first elastic support material.

In some embodiments, the measuring unit may however be detached from the first elastic support material, for example using wired connection to the one or more electrically conducting layer(s).

Method

According to the present invention, in one embodiment of the method, the measure of the circumference of the body part is a change in circumference of the body part.

In another embodiment of the method, the step of placing the first elastic support and second elastic support is done by pre-stretching the device or at least a part of it at least 20% from a relaxed dimension.

In yet another embodiment of the method, the step of monitoring is done by monitoring a data storing unit according such as a computer, a server or a handheld device.

EXAMPLE 1

An Embodiment of the Device According to the First Aspect of the Present Invention FIG. 1 shows an example of the device according to the first aspect of the present invention, where it can be seen that the device comprises a first elastic support material 1 configured for being placed around and/or on the body part, the first elastic support material having a first elastic support material length defining an longitudinal axis 2, a first elastic support material width defining a vertical axis 3. There is one or more electrically conducting layer(s) encapsulated between two elastic layers. Thus, the one or more electrically conducting layer(s) cannot be seen as they are between two layers. A measuring unit is able to be electrically connected to the one or more electrically conducting layer (s), in this case, the measuring unit is detached from the first elastic support material 1, using wired connection 4 to the one or more electrically conducting layer(s). The measuring unit, not shown here, is configured for measuring an electric property related to the one or more electrically conducting layer(s), the electric property being related to the measure of the circumference of the body part. In this example, the first elastic support material 1 comprises a surface texture adopted with a roughness similar to cotton (the first elastic support material is made of cotton) so that the first elastic support material stays in place once the first elastic support material has been placed around and/or on the body part. Further, the first elastic support width, defining the vertical axis 3, in a relaxed state, is approximately 5 cm. The first elastic support material is configured for being placed around and/or on the body part by having attachment means 5 in both ends of the longitudinal axis, such that both ends can be attached to each other (here the attachment means are on both sides, so only the attachment means in on end can be seen).

EXAMPLE 2

A First Measurement From the Measuring Unit

Figure 2:
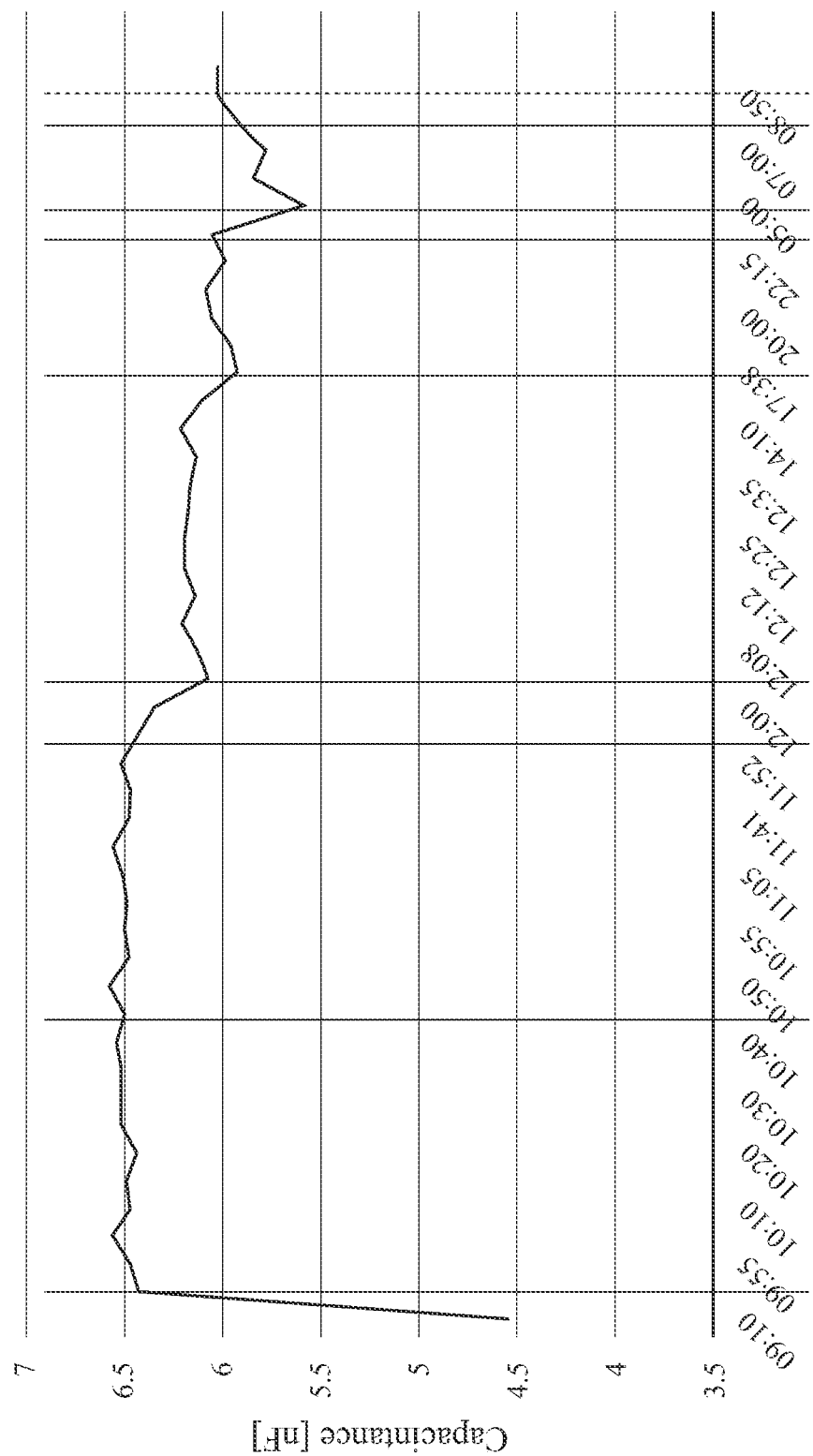
FIG. 2 shows an example of an electric property being measured using the measuring unit of the device according to the first aspect of the present invention.

FIG. 2 shows an example of an electric property being measured using the measuring unit of the device according to the first aspect of the present invention. The device has been placed around a leg during a time period of approximately 12 hours as can be seen on the times of measurement. In this example, the electric property is the capacitance, and it can be seen that in the 12 hours period the capacitance decreases as a function of the leg getting smaller as the swelling decreases. Thus, the capacitance, i.e. the electric property, is able to be related to the measure of the circumference of the body part—in this case the leg. It can be noted, that at night time i.e. from 22:15 to 5:00 when the leg is in a horizontal plane, due to the patient lying down, the leg is indeed getting smaller. In the night time, the capacitance falls from ca. 6 nF to 5.5 nF.

EXAMPLE 3

A Second Measurement From the Measuring Unit

Figure 3A:
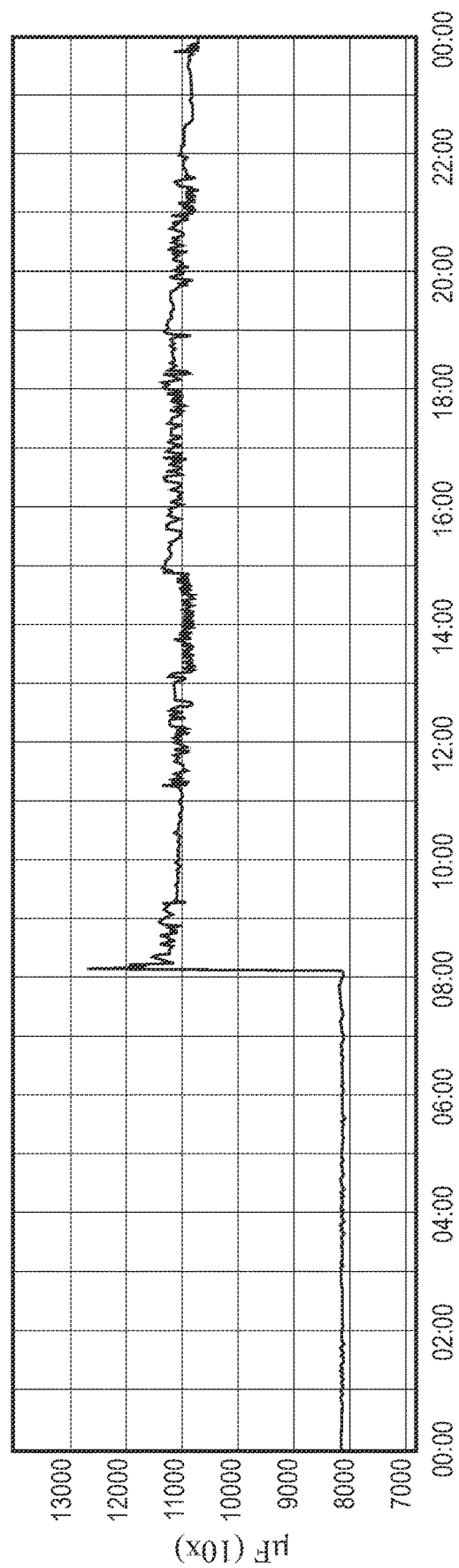
FIG. 3-8 show another example of an electric property being measured using the measuring unit of the device according to the first aspect of the present invention.

FIG. 3A shows an example of an electric property being measured during a time period of 24 hours using the measuring unit of the device according to the first aspect of the present invention.

Figure 3B:
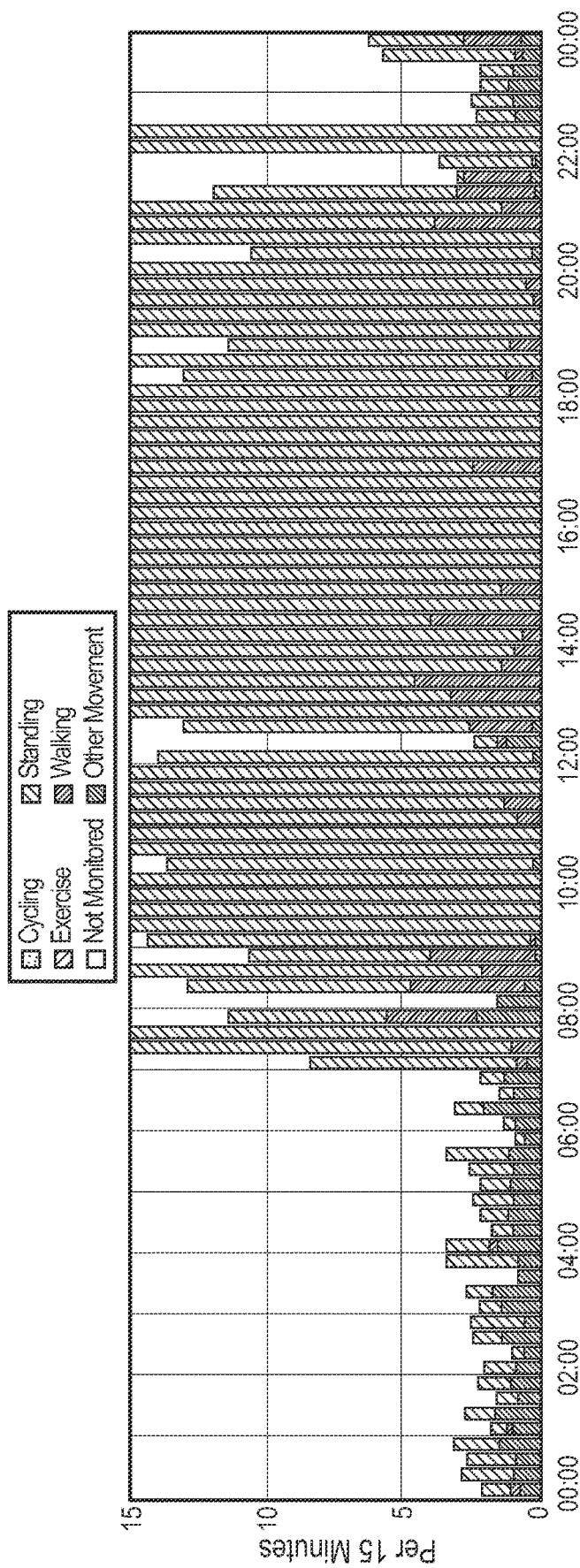

FIG. 3B shows an example of an activity log during the time period of 24 hours, wherein the 25 hours are identical to the 24 hours from FIG. 3A.

Figure 3C:
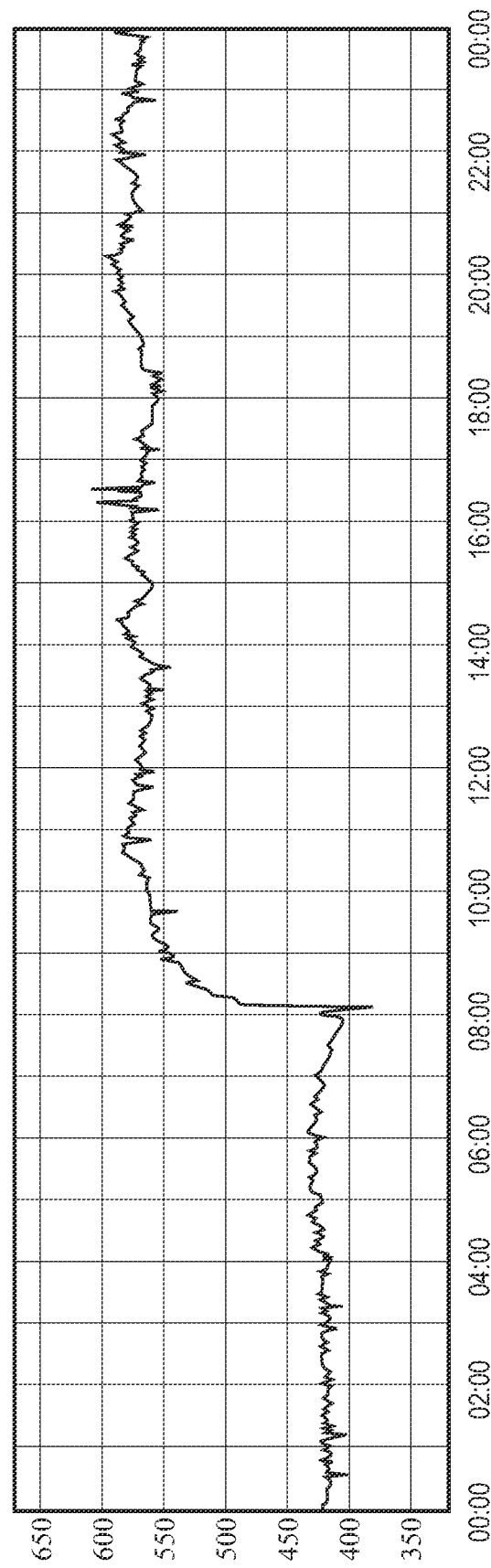
Figure 4A:
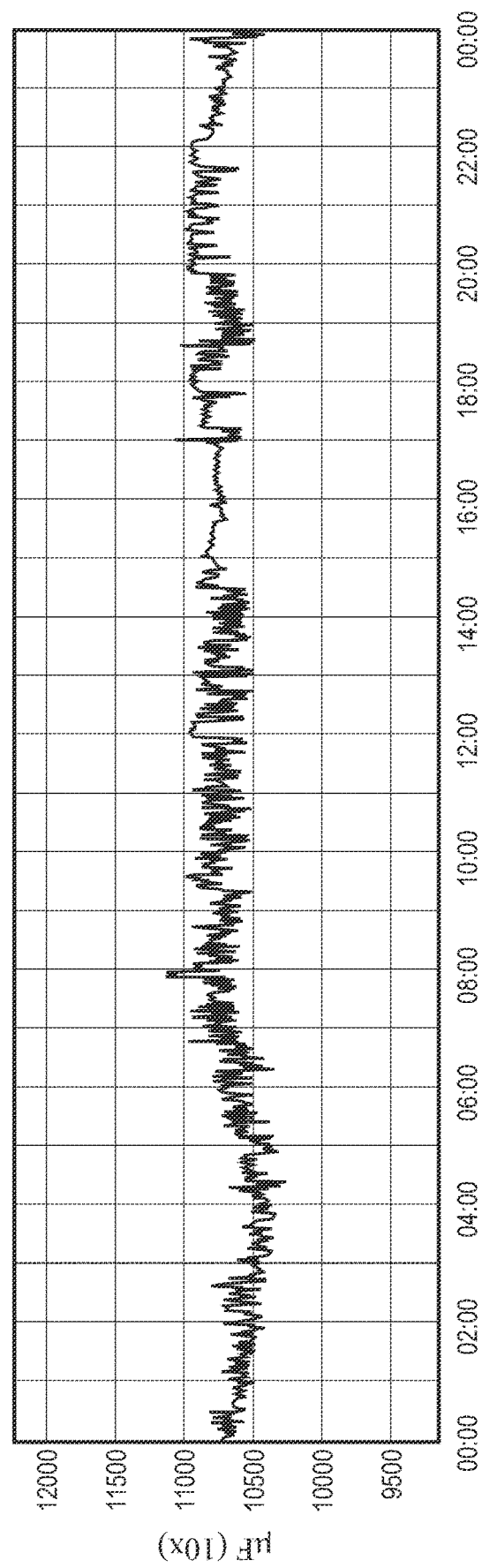
Figure 4B:
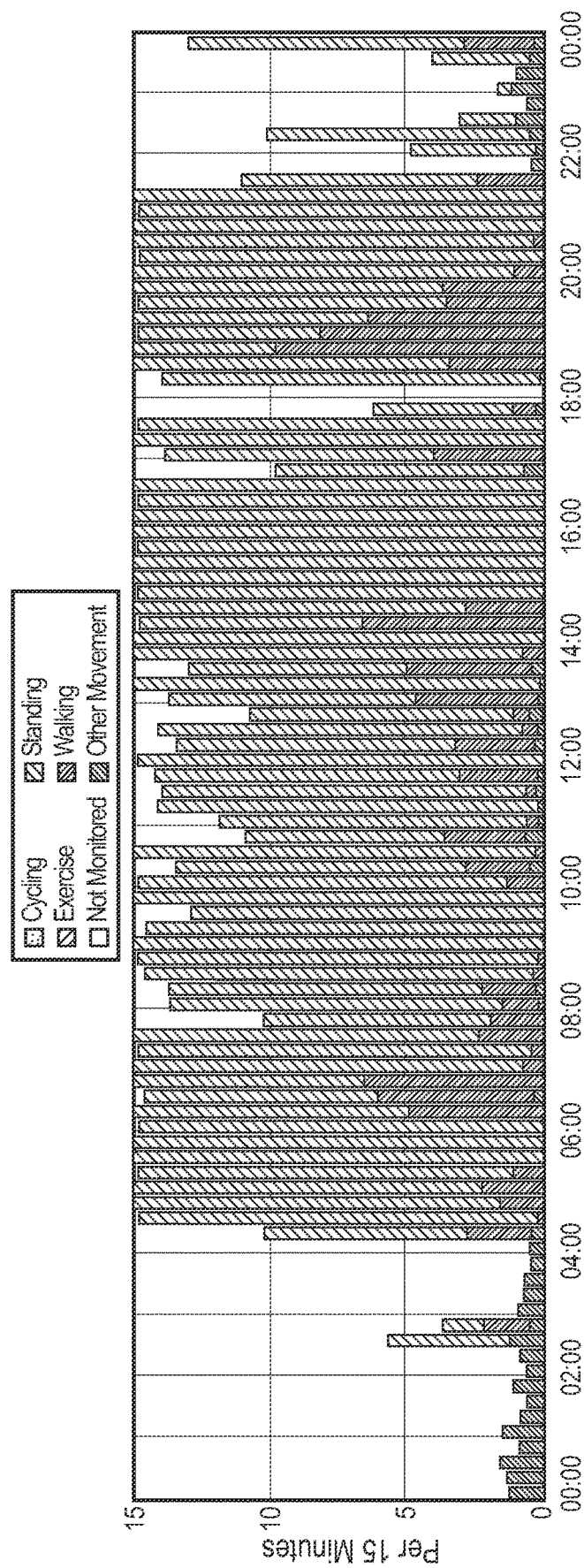
Figure 4C:
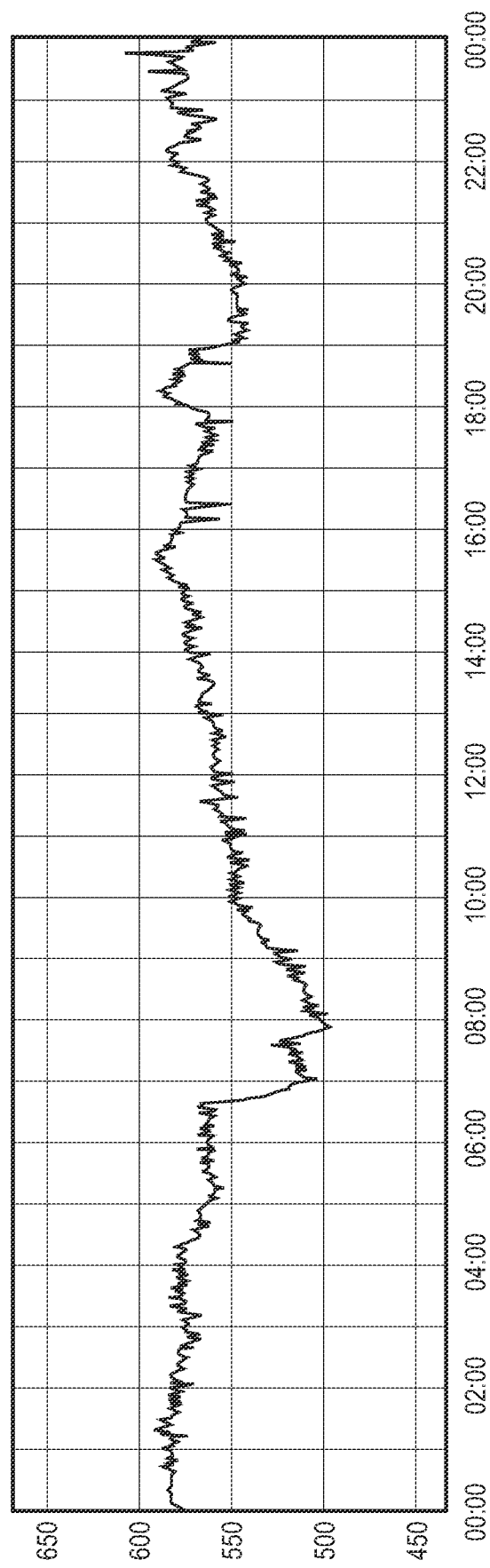
Figure 5A:
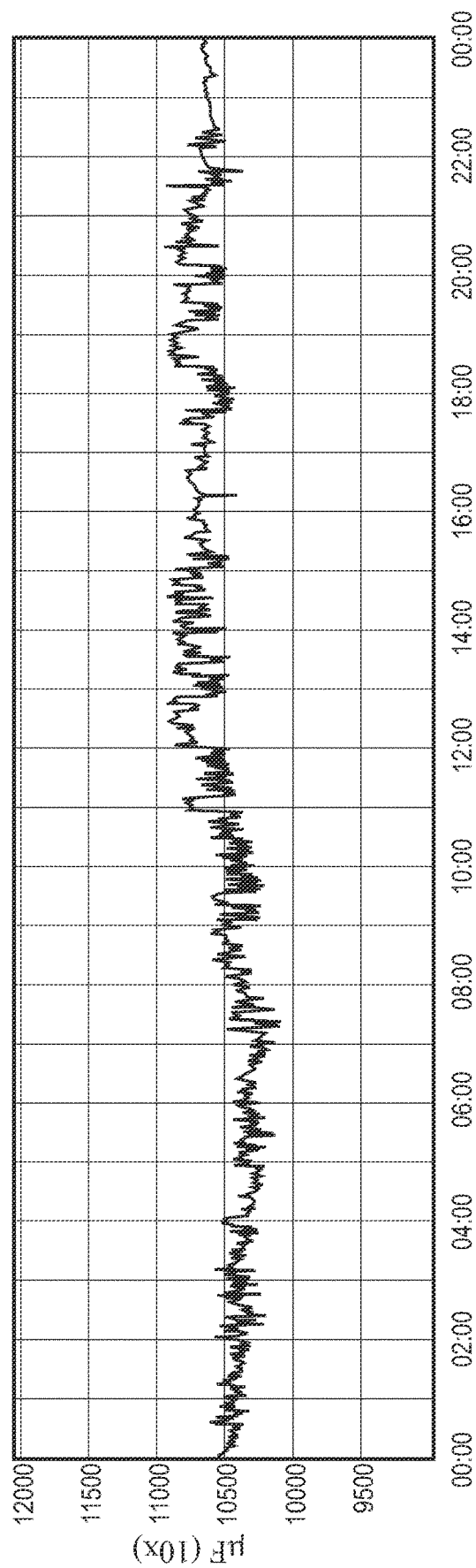
Figure 5B:
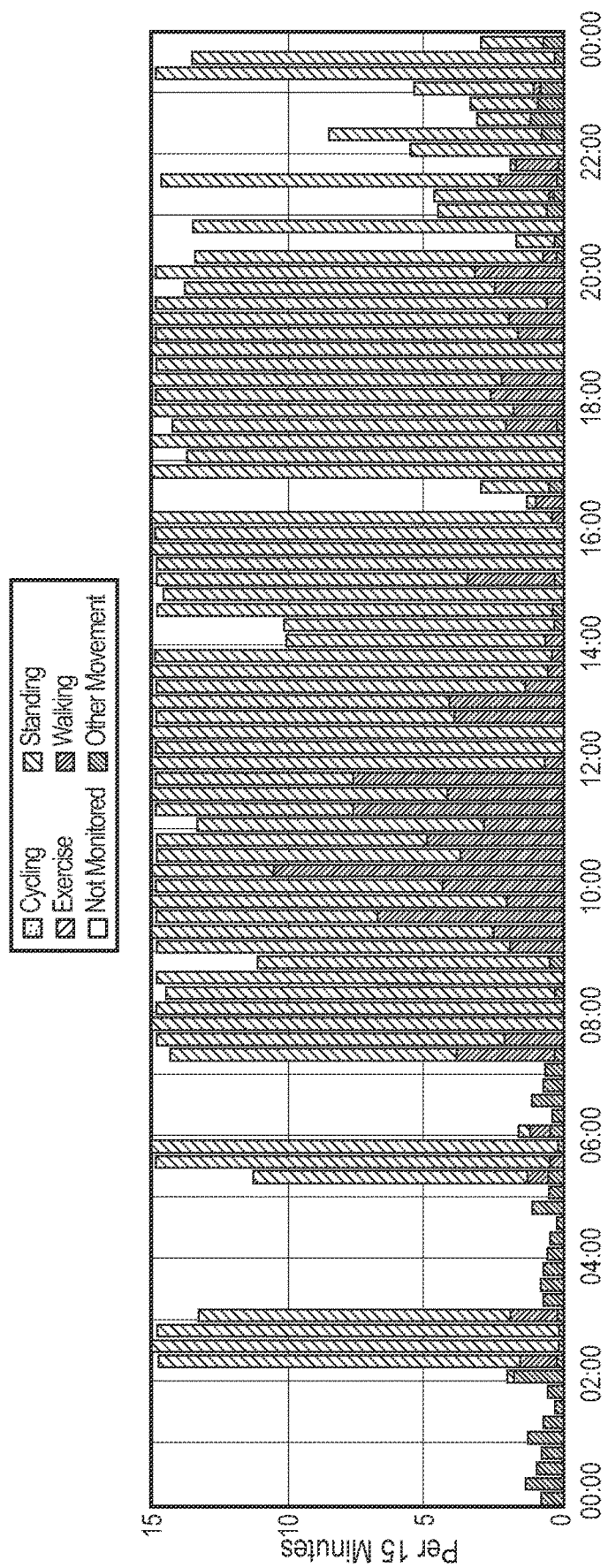
Figure 5C:
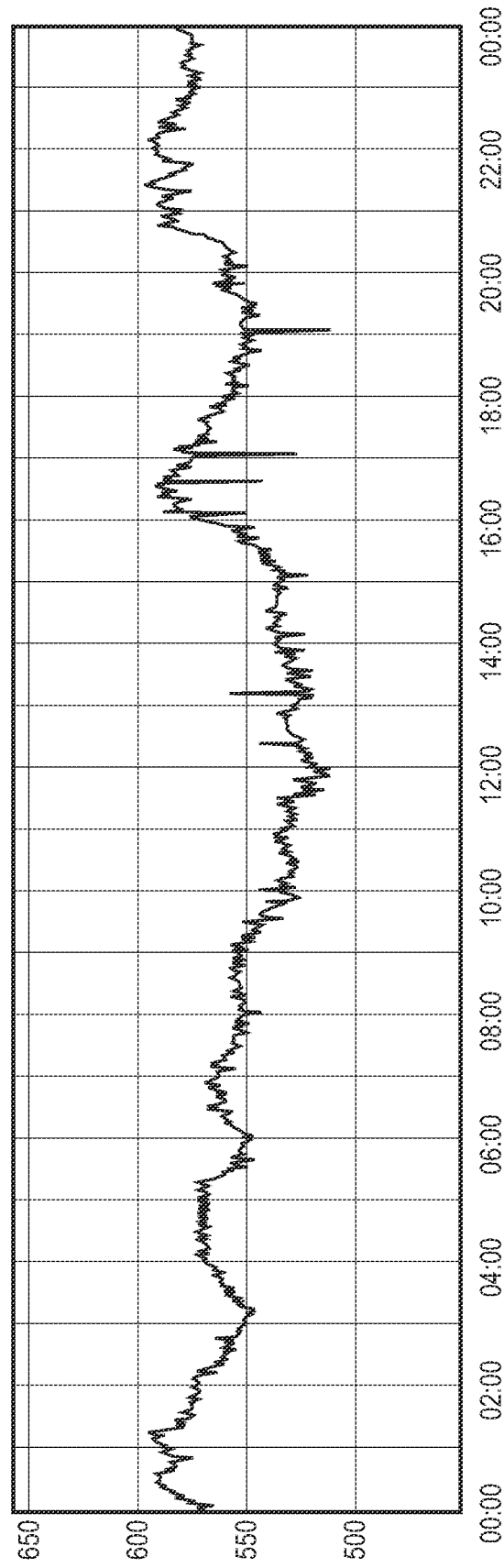
Figure 6A:
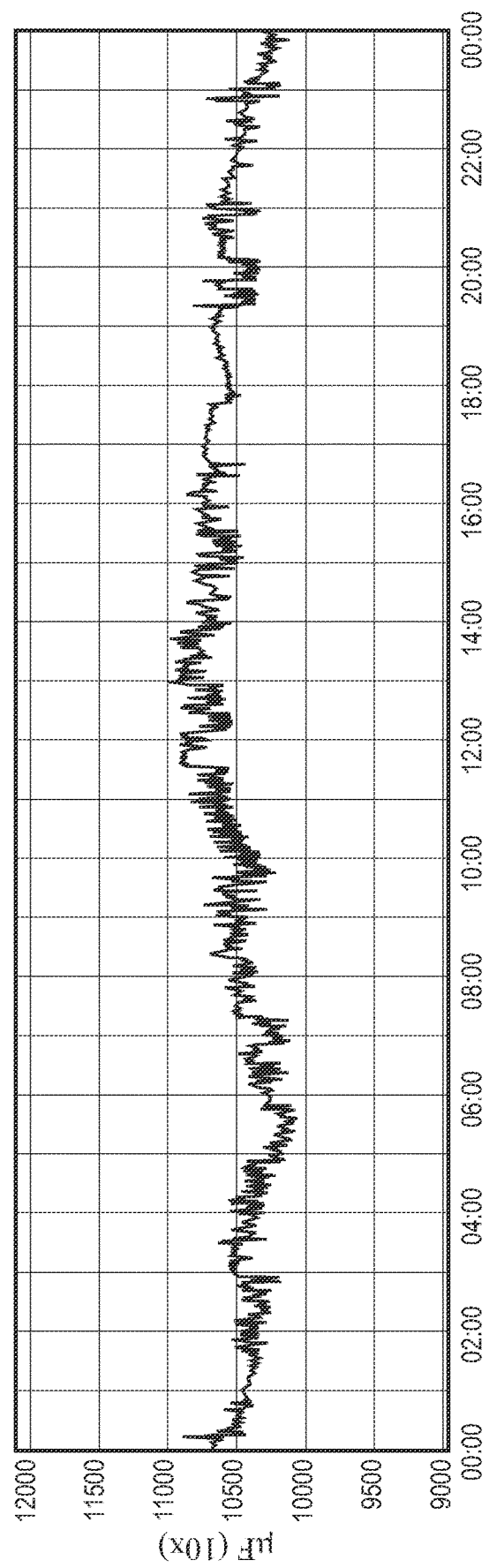
Figure 6B:
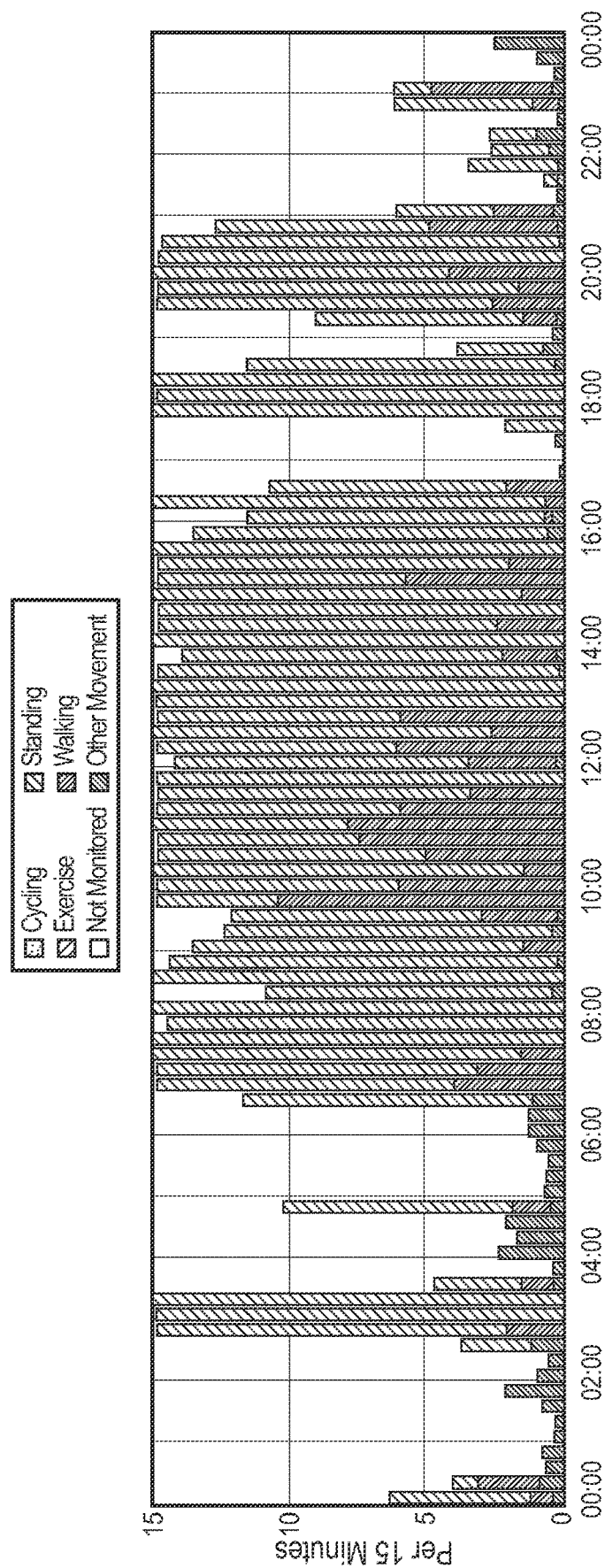
Figure 6C:
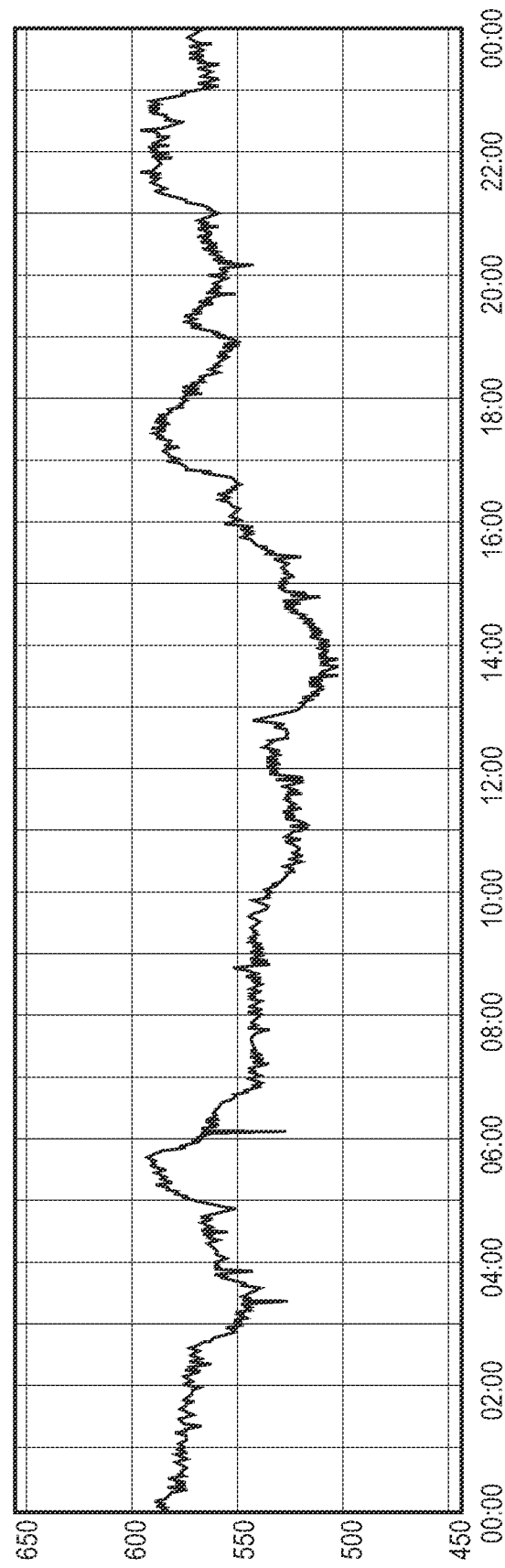
Figure 7A:
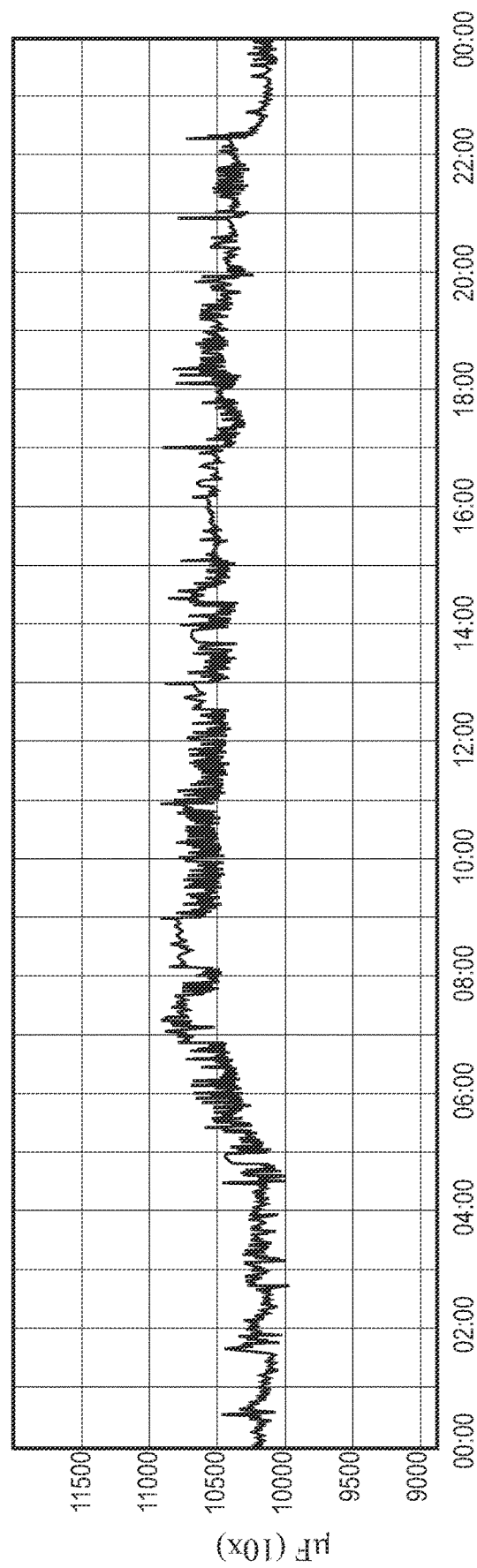
Figure 7B:
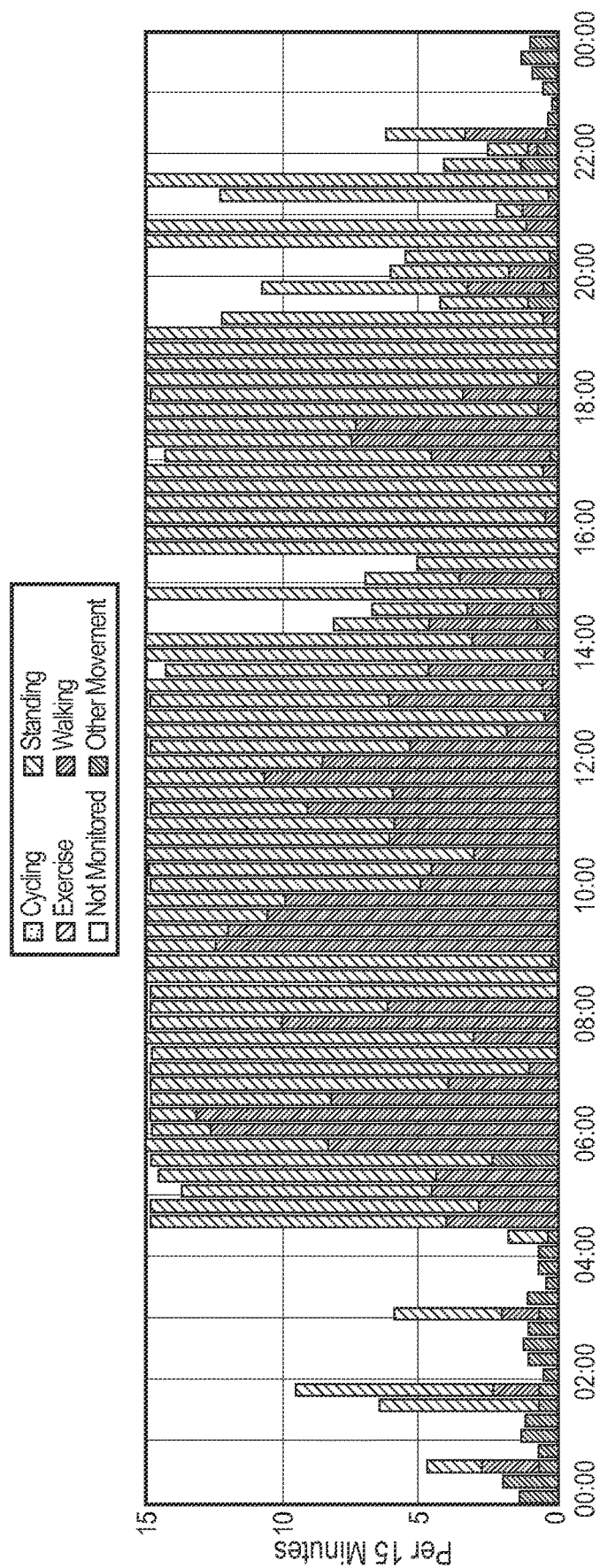
Figure 7C:
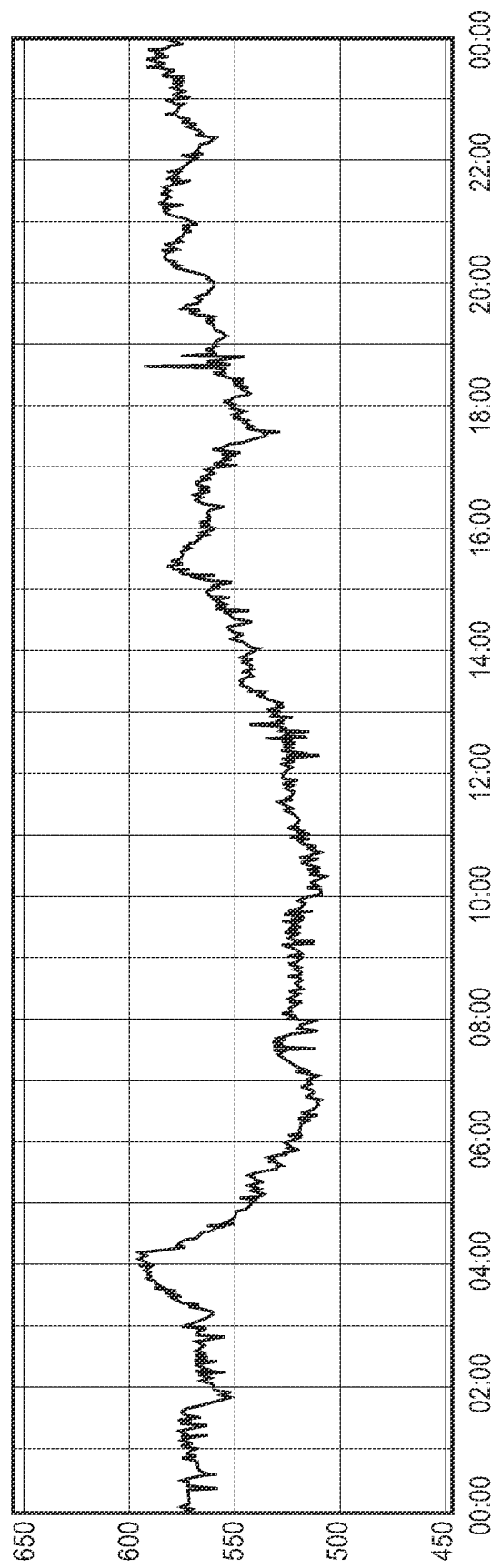
Figure 8A:
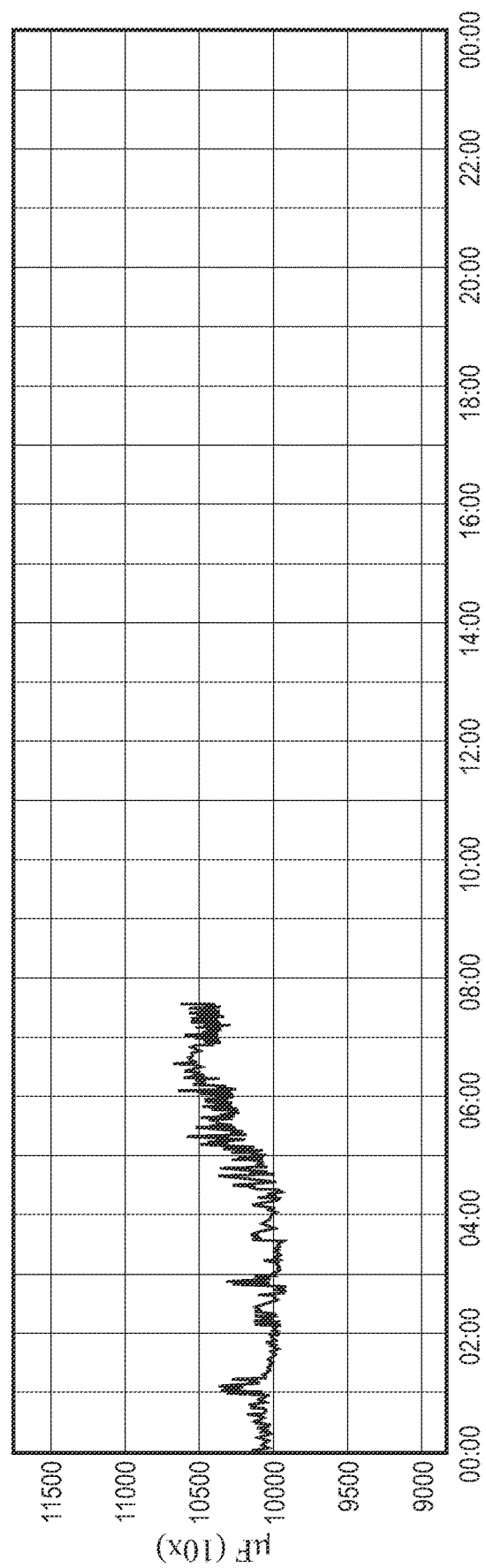
Figure 8B:
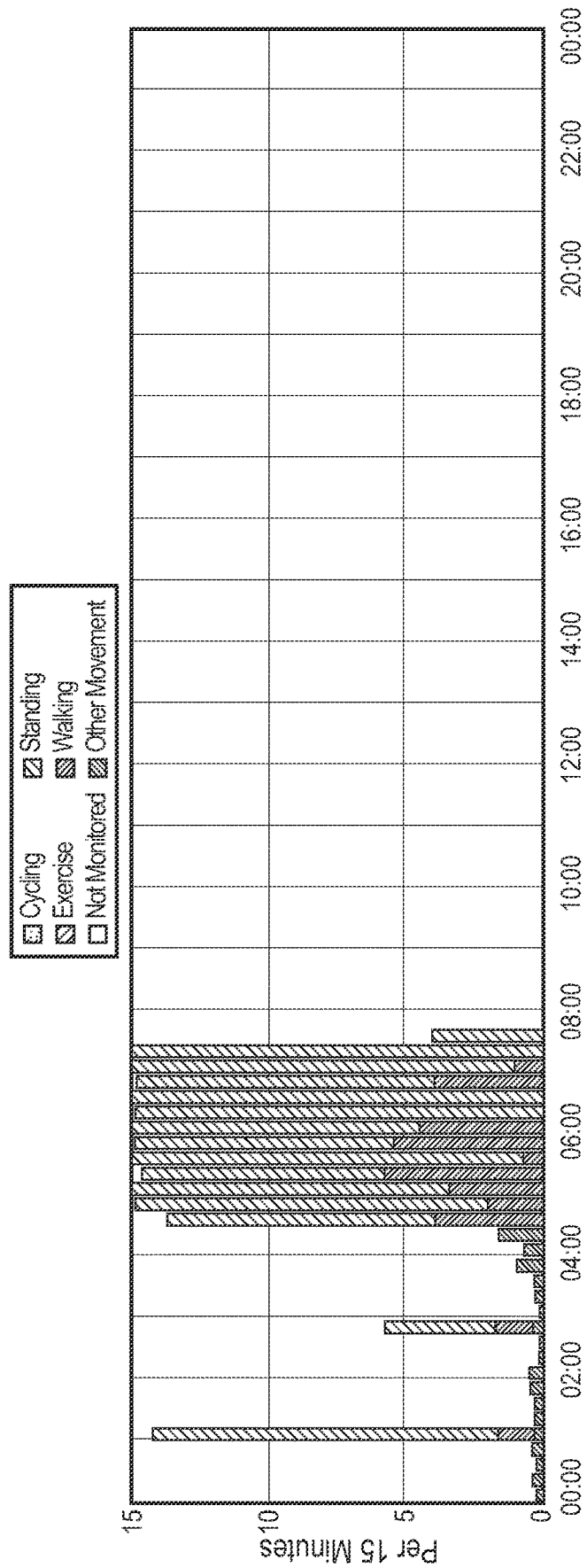
Figure 8C:
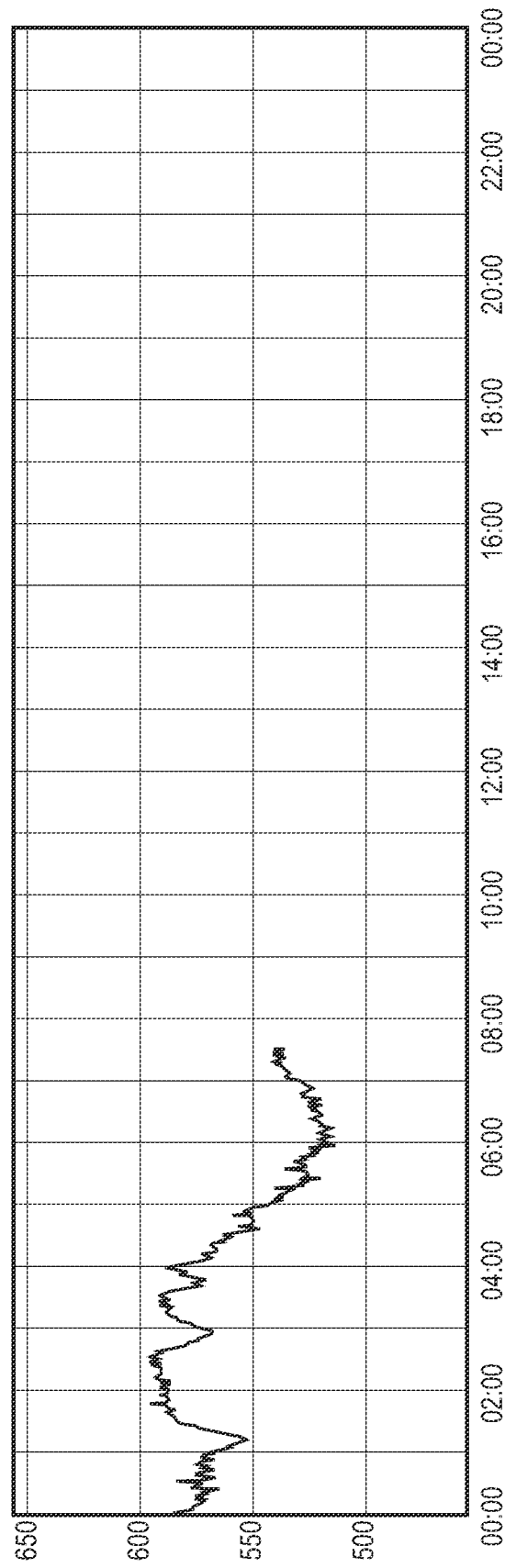

FIG. 3C shows an example of a temperature being measured during the time period of 24 hours, using a sensor to measure temperature, wherein the 25 hours are identical to the 24 hours from FIG. 3A.

The device has been placed around a leg during from the beginning of the morning at around 8:00. In this example, the electric property is the capacitance, and it can be seen that in the period from 8:00 to 0:00, the capacitance decreases as a function of the leg getting smaller as the swelling decreases. Thus, the capacitance, i.e. the electric property, is able to be related to the measure of the circumference of the body part—in this case the leg. In this example, the circumference decreases overnight approximately 3.7 cm.

In the same time period, the patient wearing the device has been told to log his/her activity during the measurement period. In this example, the log is made manually. However, in some embodiments, the device comprises an accelerometer that is configured for automatically logging an activity of the patient wearing the device.

Also in the same time period, the temperature of the patient's leg has been measured as shown in FIG. 3C. The temperature may be related to the activity of the patient and/or as an indication of inflammation in the leg.

EXAMPLE 4

Further Measurements From the Measuring Unit

FIG. 4-8 show further measurements similar to the measurements as shown in FIG. 3. The FIGS. 3-8 demonstrate that the device has been on an individual for 5 days, including 5 nights. Over the 5 nights, the circumference of the body part, in this case, a leg, has decreased by 6.3 cm. As observed from the FIGS. 3-8, the leg decreases in in circumference during night time, and increases in circumference during day time.

The first night, the circumference decreases from 57 cm to 53.3 cm. The second night, the circumference decreases to 52.4 cm. The third night, the circumference decreases to 52.1 cm. The fourth night, the circumference decreases to 51.6 cm, whereafter a new bandage is applied. The fifth night, the circumference decreases to 50.7 cm.

The invention as provided, enables that the circumference of a body part to be measured. As for the case in relation to the measurements shown in FIG. 3-8, the measurements could be used to determine, when the bandage needed to be changed, for example, as was shown, when the circumference of the leg had decreased by more than 5 cm, indicating that the bandage was no longer optimal for that particular circumference. As was shown, this was happened already after four nights. The present invention provides for a device and method that makes treatment of swelled legs more efficient. Furthermore, the experimental results have demonstrated that de-swelling is not linear. The leg swells during day time and de-swells during night time, however such that the circumference effectively decreases over several days and nights. The invention has thus provided insight into treatment of swelled legs, as has not been possible before. Accordingly, not only is a novel device disclosed herein. Novel treatments are also achieved by the use of the device as described herein.

EXAMPLE 5

Another Embodiment of the Device

Figure 9:
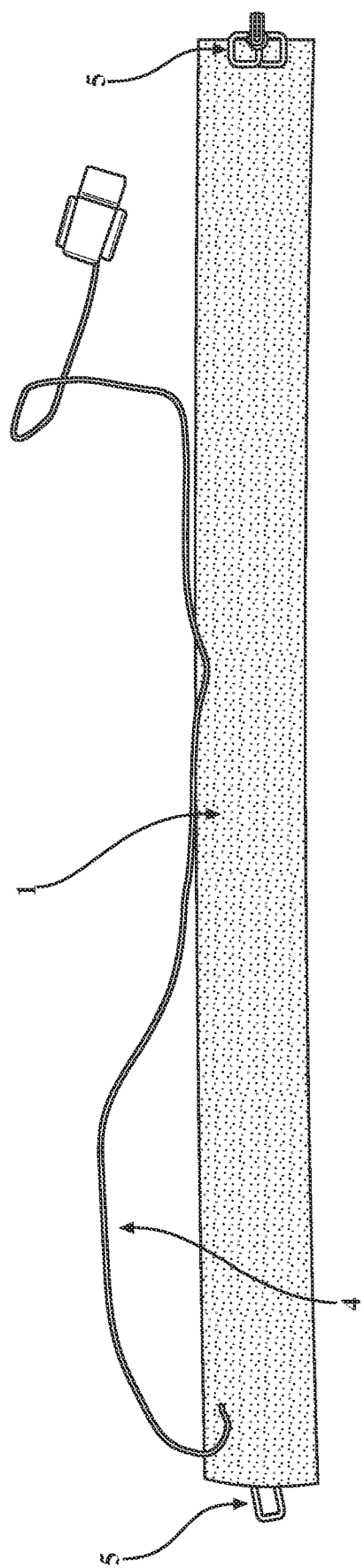
FIG. 9-10 show other embodiments of the device according to the first aspect of the present invention.

FIG. 9 shows another example of the device according to the first aspect of the present invention, where it can be seen that the device comprises a first elastic support material 1 configured for being placed around and/or on the body part, the first elastic support material having a first elastic support material length defining an longitudinal axis (2) (the axis is not shown here), a first elastic support material width defining a vertical axis 3 (the axis is not shown here). There is one or more electrically conducting layer(s) encapsulated between two elastic layers. Thus, the one or more electrically conducting layer(s) cannot be seen as they are between two layers. A measuring unit is able to be electrically connected to the one or more electrically conducting layer(s), in this case, the measuring unit is detached from the first elastic support material 1, using wired connection 4 to the one or more electrically conducting layer(s). The measuring unit, not shown here, is configured for measuring an electric property related to the one or more electrically conducting layer(s), the electric property being related to the measure of the circumference of the body part. In this example, the first elastic support material 1 comprises a surface texture adopted with a roughness similar to a material made of polyurethane fibres (the first elastic support material is made of polyurethane fibres) so that the first elastic support material stays in place once the first elastic support material has been placed around and/or on the body part. Further, the first elastic support width, defining the vertical axis 3, in a relaxed state, is approximately 1.5 cm. The first elastic support material is configured for being placed around and/or on the body part by having attachment means 5 in both ends of the longitudinal axis, such that both ends can be attached to each other.

EXAMPLE 6

Another Embodiment of the Device with a Measuring Unit

Figure 10:
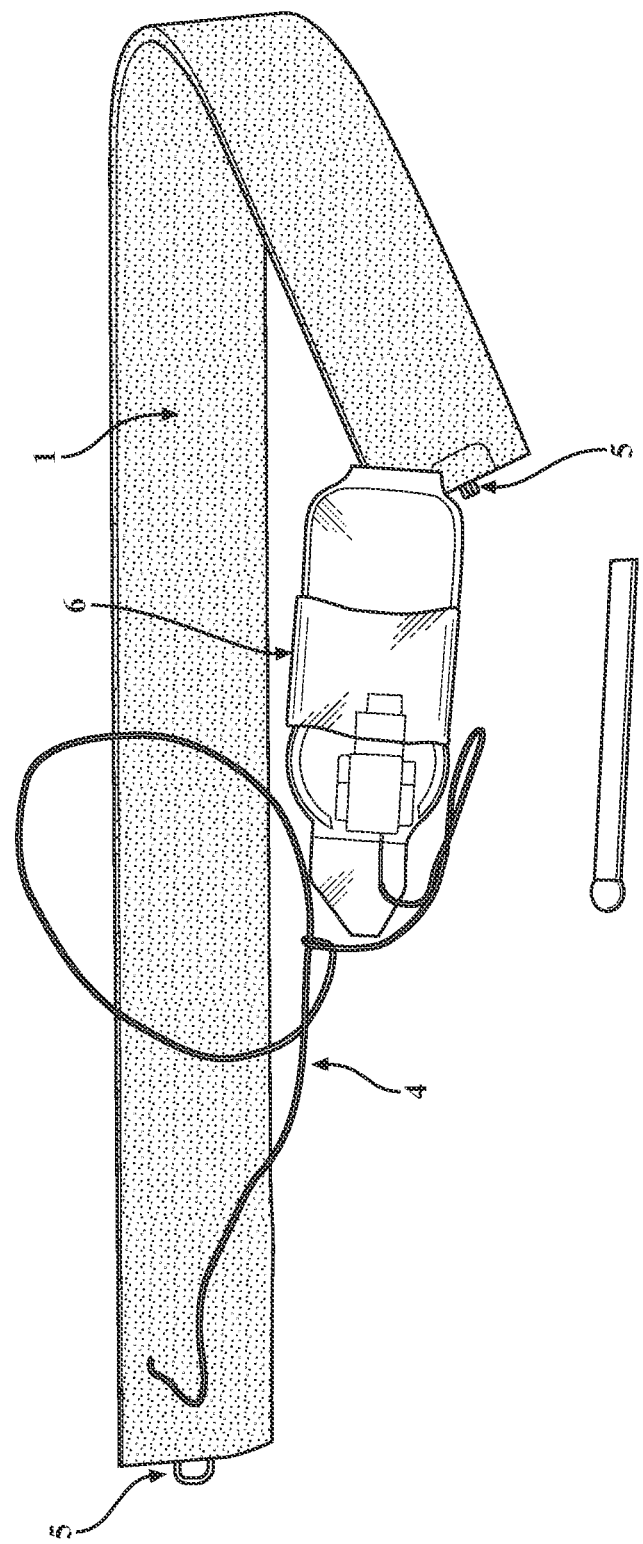

FIG. 10 shows another example of the device according to the first aspect of the present invention, now including a measuring unit 6, where it can be seen that the device comprises a first elastic support material 1 configured for being placed around and/or on the body part, the first elastic support material having a first elastic support material length defining an longitudinal axis (2) (the axis is not shown here), a first elastic support material width defining a vertical axis 3 (the axis is not shown here). There is one or more electrically conducting layer(s) encapsulated between two elastic layers. Thus, the one or more electrically conducting layer(s) cannot be seen as they are between two layers. A measuring unit is able to be electrically connected to the one or more electrically conducting layer(s), in this case, the measuring unit is detached from the first elastic support material 1, using wired connection 4 to the one or more electrically conducting layer(s). The measuring unit 6, now shown here, is configured for measuring an electric property related to the one or more electrically conducting layer(s), the electric property being related to the measure of the circumference of the body part. In this example, the first elastic support material 1 comprises a surface texture adopted with a roughness similar to a material made of polyurethane fibres (the first elastic support material is made of polyurethane fibres) so that the first elastic support material stays in place once the first elastic support material has been placed around and/or on the body part. Further, the first elastic support width, defining the vertical axis 3, in a relaxed state, is approximately 1.5 cm. The first elastic support material is configured for being placed around and/or on the body part by having attachment means 5 in both ends of the longitudinal axis, such that both ends can be attached to each other.

FIG. 11 shows a schematic cross-sectional representation, in exploded form, of a portion of the layers which may form embodiments of the present invention. A device or assembly is shown at 10, and includes various layers. The first elastic support material is shown at 1 and has an outer surface, facing upwardly in this view, and an opposed inner surface, facing downwardly in this view. Two electrically conducting layers 12 and 14 are disposed inward of the elastic support material 1. A stretchable film 16 is disposed between the electrically conducting layers 12 and 14. As discussed above, the conducting layers and stretchable film may be above or below, i.e. outward or inward, of the first elastic support material 1. In some embodiments, at least one additional elastic layer 20, which may be a second elastic support member, is provided and may encapsulate the electrical conducting layers 12 and 14 between the first elastic support material 1 and the at least one additional elastic layer 20.

The invention claimed is:
1. A device configured for management of oedema and/or lymphoedema, comprising:
a first elastic support material configured for being placed around and/or on the body part, the first elastic support material having a first elastic support material length defining an longitudinal axis, a first elastic support material width defining a vertical axis and a first elastic support material thickness defining a lateral axis, the first elastic support material having an inner surface and an opposed outer surface, the first elastic support material comprising a bandage or compression garment for managing oedema and/or lymphoedema, the first elastic support material configured to apply continuous elastic compressive pressure to the body part in an amount suitable for the management of oedema and/or lymphoedema;
two or more electrically conducting layers each located inward or outward of at least a part of the first elastic support material along at least a part of the longitudinal axis and/or along at least a part of the vertical axis, wherein the electrically conducting layers are stretchable;

a stretchable film disposed between the two or more electrically conducting layers, wherein the stretchable film deforms in a different manner than the two conducting layers; and a measuring unit that is electrically connected to the two or more electrically conducting layers, the measuring unit operable to measure an electrical capacitance of the stretchable film between the two or more electrically conducting layers and to determine and output a value of circumference or change in circumference of the body part based on a length of the two or more electrically conducting layers while the continuous elastic compressive pressure is applied, the electrical capacitance being linearly related to the value of the circumference or change in circumference.

2. The device according to claim 1, further comprising a transmitting unit configured for transmitting the value to a receiving unit or a control unit.

3. The device according to claim 2, wherein the transmitting unit transmits to the receiving unit and the receiving unit comprises a data storing unit.

4. The device according to claim 1, wherein the first elastic support material is a circular band configured to fit around the body part.

5. The device according to claim 1, further comprising a second elastic support material for being placed around or on the body part, the second elastic support material comprising a bandage or compression garment for managing the management of oedema and/or lymphoedema, the second elastic support material configured to apply continuous elastic compressive pressure to the body part, the first elastic support material being configured to be placed around or on the second elastic support material in contact with the body part in an amount suitable for the management of oedema and/or lymphoedema.

6. The device according to claim 1, wherein the device further comprises one or more non-elastic support material(s) extending from the two or more electrically conducting layers or from the first elastic support material along the longitudinal axis or along the vertical axis.

7. The device according to claim 1, wherein the first elastic support material comprises a surface texture adapted with a roughness or comprises cotton so that the first elastic support material stays in place once the first elastic support material has been placed around and/or on the body part.

8. The device according to claim 1, wherein the first elastic support material is configured for being attached to the skin of the body part.

9. The device according to claim 1, wherein the first elastic support material length, in a relaxed state, is between 15 cm and 85 cm.

10. The device according to claim 1, wherein the first elastic support material length is able to be stretched at least 20% relative to its relaxed state or wherein the first elastic support material length is able to be stretched up to 250% relative to its relaxed state.

11. The device according to claim 1, wherein the two or more electrically conducting layers have an electrically conducting layer length, in a relaxed state, that is less than 90% relative to the elastic support length.

12. The device according to claim 1, wherein the length of the two or more two or more electrically conducting layers have an electrically conducting layer length that is defined by the body part such that when the first elastic support material is placed around or on the body part, the length of the electrically conducting layer length is pre-stretched at least 20% relative to its relaxed state.

13. The device according to claim 1, wherein the two or more electrically conducting layers are separated from each other along the vertical axis.

14. The device according to claim 1, wherein the measuring unit is further configured for measuring an electric property related to the two or more electrically conducting layers layer(s), the electric property being related to temperature and/or moisture.

15. The device according to claim 1, further comprising a second elastic support material located inward or outward of the two or more electrically conducting layers, wherein the second elastic support material is configured for being in contact with the first elastic support material, thereby encapsulating the two or more electrically conducting layers in-between the first elastic support material and the second elastic support material, and such that at least part of the two or more electrically conducting layers are able to move relative to the first elastic support material or relative to the second elastic support material, the second elastic support material comprising a bandage or compression garment for managing the management of oedema and/or lymphedema, the second elastic support material configured to apply continuous elastic compressive pressure to the body part in an amount suitable for the management of oedema and/or lymphoedema.

16. The device according to claim 1, wherein the length of the two or more electrically conducting layers have an electrically conducting layer length that is able to be stretched at least 20% relative to its relaxed state.

17. The device according to claim 1, wherein the first elastic support width, in a relaxed state, is between 1 cm and 16 cm, or the two or more electrically conducting layers have a conducting layer width that, in a relaxed state and along a vertical axis, is between 2 mm and 80 mm.

18. The device according to claim 1, wherein the first elastic support material is configured with a smooth surface that is defined by its coefficient of friction, wherein the coefficient of friction is between a value of 0.2 and 0.4, and wherein the coefficient of friction is defined relative to a surface of steel.

19. The device according to claim 1, wherein the length of the two or more electrically conducting layers is a product of the capacitance and a proportionality factor, plus a constant.

20. A method for managing oedema and/or lymphedema, comprising the steps of:
providing a device configured for managing oedema and/or lymphedema, the device comprising;
a first elastic support material configured for being placed around and/or on a body part, the first elastic support material having a first elastic support material length defining an longitudinal axis, a first elastic support material width defining a vertical axis and a first elastic support material thickness defining a lateral axis, the first elastic support material having an inner surface and an opposed outer surface, the first elastic support material comprising a bandage or compression garment;
two or more electrically conducting layers each located inward or outward of at least a part of the first elastic support material along at least a part of the longitudinal axis and/or along at least a part of the vertical axis, wherein the electrically conducting layers are stretchable;
a stretchable film disposed between the two or more electrically conducting layers; and a measuring unit that is electrically connected to the two or more electrically conducting layers, the measuring unit operable to measure an electrical capacitance of the stretchable film between the two or more electrically conducting layers the electrical capacitance being linearly related to a length of the two or more electrically conducting layers;

providing a second elastic support material, the second elastic support material comprising a bandage or compression garment;

placing the first elastic support material around or on the body part;

placing the second elastic support material around or on the body part;

managing the oedema and/or lymphoedema by applying continuous elastic compressive pressure to the body part with the first and second elastic support materials, the continuous elastic compressive pressure being in an amount suitable for the management of oedema and/or lymphoedema;

wherein the step of placing the second elastic support material is done:

after the first support material is placed around the body part, such that the second elastic support material is placed around or on the first support material, or before the first support material is placed around the body part, such that the first elastic support material is placed around or on the second support material, or at the same time as the first elastic support material is placed around the first support material, such that the first support material and second support material are connected to each other; and determining and monitoring a value of a circumference or a change in circumference of the body part using the measurement of electrical capacitance based on the length of the two or more electrically conductive layers, the determining and monitoring step occurring after the first and second elastic support material have been placed and while the continuous elastic compressive pressure is applied.

21. The method according to claim 20, wherein the step of monitoring is done by monitoring a data storing unit.

22. The method according to claim 20, further comprising outputting the value of the circumference or change in circumference.

23. The method according to claim 20, wherein the length of the two or more electrically conducting layers is a product of the capacitance and a proportionality factor, plus a constant.

* * * * *